US009955905B2

(12) United States Patent
Intrator

(10) Patent No.: US 9,955,905 B2
(45) Date of Patent: May 1, 2018

(54) SYSTEMS AND METHODS FOR BRAIN ACTIVITY INTERPRETATION

(71) Applicant: NeuroSteer Ltd., Ramat Gan (IL)

(72) Inventor: Nathan Intrator, Ramat Gan (IL)

(73) Assignee: NeuroSteer Ltd., Ramat Gan (IL)

( * ) Notice: Subject to any disclaimer, the term of this patent is extended or adjusted under 35 U.S.C. 154(b) by 0 days. days.

(21) Appl. No.: 15/045,089

(22) Filed: Feb. 16, 2016

(65) Prior Publication Data
US 2016/0235351 A1 Aug. 18, 2016

Related U.S. Application Data

(60) Provisional application No. 62/116,647, filed on Feb. 16, 2015.

(51) Int. Cl.
*A61B 5/0476* (2006.01)
*A61B 5/00* (2006.01)
(Continued)

(52) U.S. Cl.
CPC ............ *A61B 5/4076* (2013.01); *A61B 5/048* (2013.01); *A61B 5/7264* (2013.01); *A61B 5/0022* (2013.01);
(Continued)

(58) Field of Classification Search
None
See application file for complete search history.

(56) References Cited

U.S. PATENT DOCUMENTS 4,638,807 A * 1/1987 Ryder ................ A61B 5/04085
600/383
4,996,989 A * 3/1991 Stundel ................ A61B 5/0416
600/383
(Continued)

FOREIGN PATENT DOCUMENTS

WO 2007138598 A1 12/2007
WO 2014027329 A1 2/2014

OTHER PUBLICATIONS

Addison, P. S. The Illustrated Wavelet Transform Handbook: Applications in Science, Engineering, Medicine and Finance. (Institute of Physics Publishing, 2002). Excerpt of chapters 3 and 6.*
(Continued)

*Primary Examiner* — Soren Harward
(74) *Attorney, Agent, or Firm* — Greenberg Traurig, LLP

(57) ABSTRACT

The present invention provides a computer-implemented method, including:

a. obtaining, in real-time, by a specifically programmed processor, electrical signal data representative of brain activity of a particular individual;
b. processing, in real-time the electrical signal data representative of brain activity of a particular individual based upon a pre-determined predictor associated with a particular brain state, selected from a library of predictors containing a plurality of pre-determined predictors, wherein each individual pre-determined predictor is associated with a unique brain state,
 wherein the pre-determined predictor associated with a particular brain state includes:
  i. a pre-determined mother wavelet,
  ii. a pre-determined representative set of wavelet packet atoms, created from the pre-determined mother wavelet,
  iii. a pre-determined ordering of wavelet packet atoms, and
  iv. a pre-determined set of normalization factors,
 wherein the processing includes:
  i. causing, by the specifically programmed processor, the electrical signal data to be deconstructed into a plurality of pre-determined deconstructed wavelet packet atoms, utilizing the pre-determined representative set of wavelet packet atoms,
   wherein time windows of the electrical signal data are projected onto the pre-determined representative set of wavelet packet atoms
    wherein the projection is via convolution or inner product, and
    wherein each pre-determined representative wavelet packet atom corresponds to a particular pre-determined brain activity feature from a library of a plurality of pre-determined brain activity features;
  ii. storing the plurality of pre-determined deconstructed wavelet packet atoms in at least one computer data object;
  iii. causing, by the specifically programmed processor, the stored plurality of pre-determined deconstructed wavelet packet atoms to be re-ordered within the computer data object, based on utilizing a pre-determined order;
  iv. obtaining a statistical measure of the activity of each of the re-ordered plurality of pre-determined deconstructed wavelet packet atoms; and
  v. normalizing the re-ordered plurality of pre-determined wavelet packet atoms, based on utilizing a pre-determined normalization factor; and
c. outputting, a visual indication of at least one personalized mental state of the particular individual, at least one personalized neurological condition of the particular individual, or both, based on the processing,
 wherein the individual pre-determined predictor associated with a particular brain state from within the plurality of pre-determined predictors is generated by the steps including:
  i. obtaining the pre-determined representative set of wavelet packet atoms by:
   a. obtaining from a plurality of individuals, by the specifically programmed processor, at least one
(Continued)

plurality of electrical signal data representative of a brain activity of a particular brain state;

b. selecting a mother wavelet from a plurality of mother wavelets,
    wherein mother wavelet is selected from an wavelet family selected from the group consisting of: Haar, Coiflet Daubehies, and Mayer wavelet families;

c. causing, by the specifically programmed processor, the at least one plurality electrical signal data to be deconstructed into a plurality of wavelet packet atoms, using the selected mother wavelet;

d. storing the plurality of wavelet packet atoms in at least one computer data object;

e. determining, an optimal set of wavelet packet atoms using the pre-determined mother wavelet, and storing the optimal set of wavelet packet atoms in at least one computer data object,
    wherein the determining is via utilizing analysis Best Basis algorithm; and f. applying, by the specifically programmed processor, wavelet denoising to the number of wavelet packet atoms in the optimal set;

ii. obtaining the pre-determined ordering of wavelet packet atoms by:

a. projecting, by the specifically programmed processor, the at least one plurality of electrical signal data representative of a brain activity for each 4 second window of the data onto the pre-determined representative set of wavelet packet atoms;

b. storing the projections in at least one computer data object;

c. determining, by the specifically programmed processor, the wire length for every data point in the projection by determining the mean absolute distance of the statistical measure of the projections of different channels from their adjacent channels;

d. storing the wire length data in at least one computer data object; and e. re-ordering the stored projections, by the specifically programmed computer to minimize a statistical value of the wire length value across each time window, and across all individuals within the plurality of individuals, and across the projections; and iii. obtaining the pre-determined set of normalization factors by:

a. determining, by the specifically programmed computer, the mean and standard deviation of the values of the stored projections.

20 Claims, 16 Drawing Sheets

(51) Int. Cl.
*A61B 5/048* (2006.01)
*A61B 5/0478* (2006.01)

(52) U.S. Cl.
CPC ........... *A61B 5/0478* (2013.01); *A61B 5/4088* (2013.01); *A61B 5/4824* (2013.01); *A61B 5/4848* (2013.01)

(56) References Cited

U.S. PATENT DOCUMENTS

| | | | |
|---|---|---|---|
| 5,999,846 A * | 12/1999 | Pardey | A61B 5/0476 600/544 |
| 6,032,064 A * | 2/2000 | Devlin | A61B 5/04004 600/372 |
| 6,052,619 A * | 4/2000 | John | A61B 5/0476 600/544 |
| 6,658,287 B1 | 12/2003 | Litt et al. | |
| 7,299,088 B1 | 11/2007 | Thakor et al. | |
| 2002/0107454 A1 | 8/2002 | Collura et al. | |
| 2003/0009096 A1 * | 1/2003 | Lahteenmaki | A61B 5/04004 600/383 |
| 2004/0028264 A1 | 2/2004 | Kalifa | |
| 2004/0030258 A1 * | 2/2004 | Williams | A61B 5/0478 600/544 |
| 2004/0127809 A1 * | 7/2004 | Kopke | A61B 5/0478 600/544 |
| 2004/0204656 A1 * | 10/2004 | Tolvanen-Laakso | A61B 5/0478 600/544 |
| 2004/0230105 A1 | 11/2004 | Geva et al. | |
| 2004/0260166 A1 * | 12/2004 | Merilainen | A61B 5/04085 600/383 |
| 2005/0149123 A1 | 7/2005 | Lesser et al. | |
| 2005/0154273 A1 * | 7/2005 | Lee | A61B 5/04085 600/393 |
| 2005/0197590 A1 | 9/2005 | Osorio et al. | |
| 2005/0228515 A1 | 10/2005 | Musallam et al. | |
| 2006/0100538 A1 * | 5/2006 | Genger | A61M 16/00 600/544 |
| 2006/0293608 A1 * | 12/2006 | Rothman | A61B 5/0476 600/545 |
| 2007/0032737 A1 * | 2/2007 | Causevic | A61B 5/048 600/544 |
| 2007/0167694 A1 * | 7/2007 | Causevic | A61B 5/0402 600/301 |
| 2007/0287930 A1 | 12/2007 | Sutton | |
| 2008/0161712 A1 | 7/2008 | Leyde | |
| 2008/0294063 A1 * | 11/2008 | Bibian | A61B 5/048 600/544 |
| 2010/0016752 A1 | 1/2010 | Sieracki | |
| 2010/0049008 A1 * | 2/2010 | Doherty | A61B 5/0476 600/301 |
| 2010/0114813 A1 * | 5/2010 | Zalay | A61B 5/048 706/58 |
| 2010/0191139 A1 * | 7/2010 | Jacquin | A61B 5/0476 600/544 |
| 2011/0130675 A1 * | 6/2011 | Bibian | A61B 5/0476 600/544 |
| 2011/0288424 A1 | 11/2011 | Kanai et al. | |
| 2011/0301433 A1 | 12/2011 | Sadowsky et al. | |
| 2011/0301487 A1 | 12/2011 | Abeyratne et al. | |
| 2012/0150545 A1 * | 6/2012 | Simon | A61B 5/0476 704/270 |
| 2012/0245481 A1 * | 9/2012 | Blanco | A61B 5/048 600/544 |
| 2013/0109995 A1 * | 5/2013 | Rothman | A61B 5/0476 600/544 |
| 2013/0310660 A1 * | 11/2013 | Zuckerman-Stark | A61B 5/02 600/301 |
| 2014/0148657 A1 | 5/2014 | Hendler et al. | |
| 2015/0265201 A1 | 9/2015 | Arbas | |
| 2015/0338917 A1 | 11/2015 | Steiner et al. | |
| 2016/0270718 A1 | 9/2016 | Heneghan et al. | |

OTHER PUBLICATIONS

Ebrahimi, F., Mikaeili, M., Estrada, E. & Nazeran, H. Automatic sleep stage classification based on EEG signals by using neural networks and wavelet packet coefficients. In IEEE Engineering in Medicine and Biology Society 2008, 1151-1154 (2008).*

Jahankhani, P., Kodogiannis, V. & Revett, K. EEG Signal Classification Using Wavelet Feature Extraction and Neural Networks. In

(56) References Cited

OTHER PUBLICATIONS

IEEE John Vincent Atanasoff International Symposium on Modern Computing 120-124 (2006).*
Lotte, F., Congedo, M., Lecuyer, A., Lamarche, F. & Arnaldi, B. A review of classification algorithms for EEG-based brain-computer interfaces. Journal of Neural Engineering 4, R1-R13 (2007).*
Subasi, A. & Gursoy, M. I. EEG signal classification using PCA, ICA, LDA and support vector machines. Expert Systems with Applications 37, 8659-8666 (2010).*
Xu, Q., Zhou, H., Wang, Y. & Huang, J. Fuzzy support vector machine for classification of EEG signals using wavelet-based features. Medical Engineering and Physics 31, 858-865 (2009).*
Xue, J.-Z., Zhang, H., Zheng, C.-X. & Yan, X.-G. Wavelet packet transform for feature extraction of EEG during mental tasks. International Conference on Machine Learning and Cybernetics 1, 2-5 (2003).*
Zalay, O. C., Kang, E. E., Cotic, M., Carlen, P. L. & Bardakjian, B. L. A wavelet packet-based algorithm for the extraction of neural rhythms. Annals of Biomedical Engineering 37, 595-613 (2009).*
Zhiwei, L. & Minfen, S. Classification of Mental Task EEG Signals Using Wavelet Packet Entropy and SVM. In International Conference on Electronic Measurement and Instruments 3:906-909 (IEEE, 2007).*
Arman, S. I., Ahmed, A. & Syed, A. Cost-Effective EEG Signal Acquisition and Recording System. International Journal of Bioscience, Biochemistry and Bioinformatics 2, 301-304 (2012).*
Gosseries, Olivia, et al., Chapter 2—Disorders of Consciousness: Coma, Vegetative and Minimally Conscious States, Springer; States of Consciousness Experimental Insights into Meditation, Waking, Sleep and Dreams, 2011, p. 29-55.
Donoho, David, De-Noising by Soft-Thresholding, IEEE Transactions on Information Theory, vol. 41, No. 3, p. 613-627, May 1995.
Coifman, Ronald, et al., Entropy-Based Algorithms for Best Basis Selection, IEEE Transactions on Information Theory, vol. 38, No. 2., p. 713-718, Mar. 1992.
Castellani, Gastone, et al. Systems Biology and Brain Activity in Neuronal Pathways by Smart Device and Advanced Signal Processing, Frontiers in Genetics, vol. 5, Article 253, p. 1-12, Aug. 2014.
Intrator, Nathan, Feature Extraction Using an Unsupervised Neural Network, Neural Computation, vol. 4, p. 98-107, 1992.
Intrator, Nathan, Combining Exploratory Projection Pursuit and Projection Pursuit Regression with Application to Neural Networks, Neural Computation, vol. 5, p. 443-455, 1993.
Stainvas, Inna, et al., Regularization of Projection Directions via Best Basis Selection Approach, International Journal of Applied Mathematics & Statistics, vol. 4, No. J06, p. 1-22, Jun. 2006.
INternational Search Report for International PCT Application PCT/IB2016/000338, dated Aug. 22, 2016.
http://www.medtronic.com/covidien/enus/products/brain-monitoring.html, 2017.
Herman, S., et al., Consensus Statement on Continuous EEG in Critically Ill Adults and Children, Part II: Personnel, Technical Specifications, and Clinical Practice, 'Journal of Clinical Neurophysiology,' vol. 32, No. 2, pp. 96-108, 2015.
Young, G. Bryan, et al., Seizure Detection with a Commercially Available Bedside EEG Monitor and the Subhairline Montage, 'Neurocritical Care Society,' pp. 411-416, 2009.
Jurcak, V., et al., 10/20, 10/10, and 10/5 systems revisited: Their validity as relative head-surface-based positioning systems, 'NeuroImage,' vol. 34, pp. 1600-1611, 2007.

* cited by examiner

Figure 3B--

SYSTEMS AND METHODS FOR BRAIN ACTIVITY INTERPRETATION

CROSS REFERENCE TO RELATED APPLICATIONS

This application claims priority to U.S. Provisional Patent Application Ser. No. 62/116,647 filed on Feb. 16, 2015, the contents of which are incorporated by reference in its entirety.

FIELD OF THE INVENTION

The field of invention relates to a method and system for monitoring the brain state, the health and wellness of subjects.

BACKGROUND OF THE INVENTION

Electroencephalography (EEG) is one method to monitor electrical activity of the brain. It is typically noninvasive, with the electrodes placed along the scalp, however, invasive electrodes may be used in specific applications. EEG measures voltage fluctuations resulting from ionic current within the neurons of the brain. However, the sensitivity of the EEG electrodes limits detection to small regions of the brain, close to each electrode, thus limiting the spatial resolution of EEG.

Functional magnetic resonance imaging (fMRI) is another method to monitor activity of the brain. However, a magnetic resonance imager is a large and expensive clinical device which can neither be used outside of the clinic, nor in a continuous manner.

BRIEF DESCRIPTION OF THE FIGURES

Some embodiments of the invention are herein described, by way of example only, with reference to the accompanying drawings. With specific reference now to the drawings in detail,ced that the particulars shown are by way of example and for purposes of illustrative discussion of embodiments of the invention. In this regard, the description taken with the drawings makes apparent to those skilled in the art how embodiments of the invention may be practiced.

FIG. 3A and FIG. 3B shows a screenshot of examples of representations of recordings for brain activity features of subjects according to some embodiments of the present invention.

SUMMARY OF THE INVENTION

Figure 1:
FIG. 1 shows a screenshot of recording electrodes according to some embodiments of the present invention.

In one embodiment, the present invention provides a computer implemented method including:
a. obtaining, in real-time, by a specifically programmed processor, electrical signal data representative of brain activity of a particular individual;
b. processing, in real-time the electrical signal data representative of brain activity of a particular individual based upon a pre-determined predictor associated with a particular brain state, selected from a library of predictors containing a plurality of pre-determined predictors, wherein each individual pre-determined predictor is associated with a unique brain state,
wherein the pre-determined predictor associated with a particular brain state includes:
i. a pre-determined mother wavelet,
ii. a pre-determined representative set of wavelet packet atoms, created from the pre-determined mother wavelet,
iii. a pre-determined ordering of wavelet packet atoms, and
iv. a pre-determined set of normalization factors,
wherein the processing includes:
i. causing, by the specifically programmed processor, the electrical signal data to be deconstructed into a plurality of pre-determined deconstructed wavelet packet atoms, utilizing the pre-determined representative set of wavelet packet atoms,
wherein time windows of the electrical signal data are projected onto the pre-determined representative set of wavelet packet atoms
wherein the projection is via convolution or inner product, and
wherein each pre-determined representative wavelet packet atom corresponds to a particular pre-determined brain activity feature from a library of a plurality of pre-determined brain activity features;
ii. storing the plurality of pre-determined deconstructed wavelet packet atoms in at least one computer data object;
iii. causing, by the specifically programmed processor, the stored plurality of pre-determined deconstructed wavelet packet atoms to be re-ordered within the computer data object, based on utilizing a pre-determined order;
iv. obtaining a statistical measure of the activity of each of the re-ordered plurality of pre-determined deconstructed wavelet packet atoms; and
v. normalizing the re-ordered plurality of pre-determined wavelet packet atoms, based on utilizing a pre-determined normalization factor; and c. outputting, a visual indication of at least one personalized mental state of the particular individual, at least one personalized neurological condition of the particular individual, or both, based on the processing, wherein the individual pre-determined predictor associated with a particular brain state from within the plurality of pre-determined predictors is generated by the steps including:

i. obtaining the pre-determined representative set of wavelet packet atoms by:
   a. obtaining from a plurality of individuals, by the specifically programmed processor, at least one plurality of electrical signal data representative of a brain activity of a particular brain state;
   b. selecting a mother wavelet from a plurality of mother wavelets,
      wherein mother wavelet is selected from an wavelet family selected from the group consisting of: Haar, Coiflet Daubehies, and Mayer wavelet families;
   c. causing, by the specifically programmed processor, the at least one plurality electrical signal data to be deconstructed into a plurality of wavelet packet atoms, using the selected mother wavelet;
   d. storing the plurality of wavelet packet atoms in at least one computer data object;
   e. determining, an optimal set of wavelet packet atoms using the pre-determined mother wavelet, and storing the optimal set of wavelet packet atoms in at least one computer data object,
      wherein the determining is via utilizing analysis Best Basis algorithm; and
   f. applying, by the specifically programmed processor, wavelet denoising to the number of wavelet packet atoms in the optimal set;

ii. obtaining the pre-determined ordering of wavelet packet atoms by:
   a. projecting, by the specifically programmed processor, the at least one plurality of electrical signal data representative of a brain activity for each 4 second window of the data onto the pre-determined representative set of wavelet packet atoms;
   b. storing the projections in at least one computer data object;
   c. determining, by the specifically programmed processor, the wire length for every data point in the projection by determining the mean absolute distance of the statistical measure of the projections of different channels from their adjacent channels;
   d. storing the wire length data in at least one computer data object; and
   e. re-ordering the stored projections, by the specifically programmed computer to minimize a statistical value of the wire length value across each time window, and across all individuals within the plurality of individuals, and across the projections; and iii. obtaining the pre-determined set of normalization factors by:
   a. determining, by the specifically programmed computer, the mean and standard deviation of the values of the stored projections.

In one embodiment, the present invention provides a specifically programmed computer system including:

a. at least one specialized computer machine including:
   i. a non-transient memory, electronically storing particular computer executable program code; and
   ii. at least one computer processor which, when executing the particular program code, becomes a specifically programmed computer processor configured to perform at least the following operations:
      1. obtaining, in real-time, by a specifically programmed processor, electrical signal data representative of brain activity of a particular individual;
      2. processing, in real-time the electrical signal data representative of brain activity of a particular individual based upon an individual pre-determined predictor associated with a particular brain state, selected from a library of predictors containing a plurality of pre-determined predictors, wherein each individual pre-determined predictor is associated with a unique brain state,
         wherein the pre-determined predictor associated with a particular brain state comprises:
            i. a pre-determined mother wavelet,
            ii. a pre-determined representative set of wavelet packet atoms,
            iii. a pre-determined ordering of wavelet packet atoms, created from the pre-determined mother wavelet, and
            iv. a pre-determined set of normalization factors,
         wherein the processing comprises:
            i. causing, by the specifically programmed processor, the electrical signal data to be deconstructed into a plurality of pre-determined deconstructed wavelet packet atoms, utilizing the pre-determined representative set of wavelet packet atoms,
               wherein time windows of the electrical signal data are projected onto the pre-determined representative set of wavelet packet atoms
                  wherein the projection is via convolution or inner product, and
               wherein each pre-determined representative wavelet packet atom corresponds to a particular pre-determined brain activity feature from a library of a plurality of pre-determined brain activity features;
            ii. storing the plurality of pre-determined deconstructed wavelet packet atoms in at least one computer data object;
            iii. causing, by the specifically programmed processor, the stored plurality of pre-determined deconstructed wavelet packet atoms to be re-ordered within the computer data object, based on utilizing a pre-determined order;
iv. obtaining a statistical measure of the activity of each of the re-ordered plurality of pre-determined deconstructed wavelet packet atoms; and
v. normalizing the re-ordered plurality of pre-determined wavelet packet atoms, based on utilizing a pre-determined normalization factor; and
3. outputting, a visual indication of at least one personalized mental state of the particular individual, at least one personalized neurological condition of the particular individual, or both, based on the processing,
wherein an individual pre-determined predictor associated with a particular brain state within the plurality of pre-determined predictors is generated by the steps consisting of:
  i. obtaining the pre-determined representative set of wavelet packet atoms by:
    1. obtaining from a plurality of individuals, by the specifically programmed processor, at least one plurality of electrical signal data representative of a brain activity of a particular brain state;
    2. selecting a mother wavelet from a plurality of mother wavelets,
      wherein mother wavelet is selected from an wavelet family selected from the group consisting of: Haar, Coiflet Daubehies, and Mayer wavelet families;
    3. causing, by the specifically programmed processor, the at least one plurality electrical signal data to be deconstructed into a plurality of wavelet packet atoms, using the selected mother wavelet;
    4. storing the plurality of wavelet packet atoms in at least one computer data object;
    5. determining, an optimal set of wavelet packet atoms using the pre-determined mother wavelet, and storing the optimal set of wavelet packet atoms in at least one computer data object,
      wherein the determining is via utilizing a Best Basis algorithm; and
    6. applying, by the specifically programmed processor, wavelet denoising to the number of wavelet packet atoms in the optimal set;
  ii. obtaining the pre-determined ordering of wavelet packet atoms by:
    1. projecting, by the specifically programmed processor, the at least one plurality of electrical signal data representative of a brain activity for each 4 second window of the data onto the pre-determined representative set of wavelet packet atoms;
    2. storing the projections in at least one computer data object;
    3. determining, by the specifically programmed processor, the wire length for every data point in the projection by determining the mean absolute distance of the statistical measure of the projections of different channels from their adjacent channels;
    4. storing the wire length data in at least one computer data object; and
    5. re-ordering the stored projections, by the specifically programmed computer to minimize a statistical value of the wire length value across each time window, and across all individuals within the plurality of individuals, and across the projections; and
  iii. obtaining the pre-determined set of normalization factors by:
    1. determining, by the specifically programmed computer, the mean and standard deviation of the values of the stored projections.

In one embodiment, the electrical signal data representative of brain activity of a particular individual is recorded using two electrodes located on the forehead of the particular individual.

In one embodiment, each time window is a four second time window.

In one embodiment, the statistical value for the re-ordering is selected from the group consisting of: the mean of the sum of the absolute differences of the wavelet packet atoms, and a mean of the sum of (1−correlation) of the wavelet packet atoms.

In one embodiment, the visual indication of at least one personalized mental state of the particular individual is used to identify an underlying mental state, an underlying neurological condition, or a combination of an underlying mental state and an underlying neurological condition, in the particular individual, wherein the specifically programmed computer utilizes at least one machine learning algorithm include, but is not limited to logistic regression modeling, support vector machine modeling, and a deep learning modeling, to assign at least one specific brain state to the visual indication of at least one personalized mental state of the particular individual, wherein the at least one specific brain state is associated with a mental state, a neurological condition, or a combination of a mental state and a neurological condition.

In one embodiment, the assignment of at least one specific brain state to the visual indication of at least one personalized mental state of the particular individual identifies an abnormality in at least one neural network in the brain of the particular individual associated with a particular neurological condition.

In one embodiment, the abnormality in at least one neural network in the brain of the particular individual is used to diagnose the particular individual having a neurological condition.

In one embodiment, the neurological condition is selected from the group consisting of, Alzheimer's disease, dementia, stress, fatigue, anxiety, epilepsy, traumatic brain injury, loss of cognitive function, migraine, chronic pain, coma, a lack of response, or inappropriate response to external stimuli associated with autism, or autism spectrum disorders, a lack of concentration, and sleep disorders.

In one embodiment, the at least one specific brain state is used to determine the emotional state of the particular individual.

In one embodiment, the particular individual is receiving a therapy, and the visual indication of at least one personalized mental state of the particular individual is used to determine the effectiveness of the therapy.

In one embodiment, the particular individual is receiving a therapy, and the visual indication of at least one personalized mental state of the particular individual is used to determine the nature of the therapy to be administered.

In one embodiment, the particular individual is receiving a therapy, and the visual indication of at least one personalized mental state of the particular individual is used to determine the duration of the therapy.

In one embodiment, the particular individual is receiving a therapy, and the visual indication of at least one personalized mental state of the particular individual is used to determine the dosing regimen of the therapy.

In one embodiment, the therapy is an anesthetic agent, and the effectiveness of the anesthetic is determined by the particular individual's ability to feel pain and/or the individual's perceived pain level and the correlation to the change in the visual indication of at least one personalized mental state of the particular individual.

In one embodiment, the therapy is a migraine therapy, and the effectiveness of the migraine therapy is determined by the particular individual's ability to feel pain, and/or the individual's perceived pain level and the correlation to the change in the visual indication of at least one personalized mental state of the particular individual.

In one embodiment, the particular individual is performing a specific cognitive task.

In one embodiment, the specific cognitive task is selected from the group including short and/or long term memory recall, e-learning, meditation, and concentration.

In one embodiment, the particular individual has a particular brain state at a certain time.

DETAILED DESCRIPTION OF THE INVENTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. In some embodiments, the terms "instantaneous," "instantaneously," "instantly," and "in real time" refer to a condition where a time difference between a first time when a search request is transmitted and a second time when a response to the request is received is no more than 1 second. In some embodiments, the time difference between the request and the response is between less than 1 second and several seconds.

As used herein, the term "dynamic(ly)" means that events and/or actions can be triggered and/or occur without any human intervention. In some embodiments, events and/or actions in accordance with the present invention can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

Decomposing EEG signals into different components is an effective tool to study brain activity and brain states, and deducing the role of certain functional regions of the brain, or neural networks in the brain for a given brain state. Without being limited by any particular theory, a particular brain state is associated with a particular mental state, a particular neurological condition, or a particular combination of a mental state and a neurological condition.

Without being intended to be limited by any particular theory, brain activity, detected via conventional EEG, is associated with a number of frequency bands from around 0.5 Hz (Delta waves) to Gamma waves which are above 32 Hz. In between are Theta, Alpha, and Beta waves, among others. However, it is assumed EEG electrodes are only sensitive to electrical signals which emanate from a small region of the brain, close to each electrode. Consequently, it is customary to record EEG activity with a large number of electrodes which cover the whole head. The location of the brain responsible for the detected electrical activity is calculated by estimating the phase of the electrical signal as it arrives to different electrodes. The BAFs described above may include these frequency bands as well.

In some embodiments of the present invention, the determining the role of certain regions or neural networks within the brain for a given cognitive function or mental state is not required. In some embodiments, the electrical activity of the brain of a subject is recorded using two electrodes (e.g., Fp1 and Fp2) located on the forehead of the subject. In some embodiments, either the Fp1, or the Fp2 electrode is used as a reference electrode, and the recorded electrical activity is the difference in between the Fp1 and Fp2 electrode. Alternatively, in some embodiments, the FpZ electrode may be used as either the reference, or recording electrode.

In some embodiments, the present invention provides a computer implemented method including:
  a. obtaining, in real-time, by a specifically programmed processor, electrical signal data representative of brain activity of a particular individual;
  b. processing, in real-time the electrical signal data representative of brain activity of a particular individual based upon a pre-determined predictor associated with a particular brain state, selected from a library of predictors containing a plurality of pre-determined predictors, wherein each individual pre-determined predictor is associated with a unique brain state,
    wherein the pre-determined predictor associated with a particular brain state includes:
      i. a pre-determined mother wavelet,
      ii. a pre-determined representative set of wavelet packet atoms, created from the pre determined mother wavelet,
      iii. a pre-determined ordering of wavelet packet atoms, and
      iv. a pre-determined set of normalization factors, wherein the processing includes:
  i. causing, by the specifically programmed processor, the electrical signal data to be deconstructed into a plurality of pre-determined deconstructed wavelet packet atoms, utilizing the pre-determined representative set of wavelet packet atoms,
     wherein time windows of the electrical signal data are projected onto the pre-determined representative set of wavelet packet atoms
       wherein the projection is via convolution or inner product, and
     wherein each pre-determined representative wavelet packet atom corresponds to a particular pre-determined brain activity feature from a library of a plurality of pre-determined brain activity features;
  ii. storing the plurality of pre-determined deconstructed wavelet packet atoms in at least one computer data object;
  iii. optionally causing, by the specifically programmed processor, the stored plurality of pre-determined deconstructed wavelet packet atoms to be re-ordered within the computer data object, based on utilizing a pre-determined order;
  iv. obtaining a statistical measure of the activity of each of the re-ordered plurality of pre-determined deconstructed wavelet packet atoms; and
  v. normalizing the re-ordered plurality of pre-determined wavelet packet atoms, based on utilizing a pre-determined normalization factor; and
     a. outputting, a visual indication of at least one personalized mental state of the particular individual, at least one personalized neurological condition of the particular individual, or both, based on the processing,
wherein the individual pre-determined predictor associated with a particular brain state from within the plurality of pre-determined predictors is generated by the steps including:
  i. obtaining the pre-determined representative set of wavelet packet atoms by:
     a. obtaining from a plurality of individuals, by the specifically programmed processor, at least one plurality of electrical signal data representative of a brain activity of a particular brain state;
     b. selecting a mother wavelet from a plurality of mother wavelets,
        wherein mother wavelet is selected from an wavelet family selected from the group consisting of: Haar, Coiflet Daubehies, and Mayer wavelet families;
     c. causing, by the specifically programmed processor, the at least one plurality electrical signal data to be deconstructed into a plurality of wavelet packet atoms, using the selected mother wavelet;
     d. storing the plurality of wavelet packet atoms in at least one computer data object;
     e. determining, an optimal set of wavelet packet atoms using the pre-determined mother wavelet, and storing the optimal set of wavelet packet atoms in at least one computer data object,
        wherein the determining is via utilizing a Best Basis algorithm; and
     f. applying, by the specifically programmed processor, wavelet denoising to the number of wavelet packet atoms in the optimal set;
  ii. obtaining the pre-determined ordering of wavelet packet atoms by:
     a. projecting, by the specifically programmed processor, the at least one plurality of electrical signal data representative of a brain activity for each 4 second window of the data onto the pre-determined representative set of wavelet packet atoms;
     b. storing the projections in at least one computer data object;
     c. determining, by the specifically programmed processor, the wire length for every data point in the projection by determining the mean absolute distance of the statistical measure of the projections of different channels from their adjacent channels;
     d. storing the wire length data in at least one computer data object; and
     e. optionally re-ordering the stored projections, by the specifically programmed computer to minimize a statistical value of the wire length value across each time window, and across all individuals within the plurality of individuals, and across the projections; and
  iii. obtaining the pre-determined set of normalization factors by:
     a. determining, by the specifically programmed computer, the mean and standard deviation of the values of the stored projections.

In some embodiments, the electrical signal data representative of brain activity of a particular individual is recorded using two electrodes located on the forehead of the particular individual.

An example of recording electrodes according to some embodiments of the present invention is shown in FIG. 1. In some embodiments, the electrical activity of the brain of a subject is recorded using between one and three electrodes located on the forehead of the subject. In some embodiments, the electrical activity of the brain of a subject is recorded using between one and three electrodes located at region(s) of the head which is/are other than or in addition to the forehead of the subject. For example, in some embodiments, at least one electrode is located behind or on, or in an ear of the subject. For example, in some embodiments, at least one electrode is part of an item position on the head of the subject, where the item is configured for at least one additional function in addition to hosting the at least one electrode. For example, in some embodiments, the item is a headwear piece (e.g., hat). For example, in some embodiments, the item is an electronic device (e.g., headphones).

In some embodiments, the electrical activity of the brain of a subject is recorded according to the methods disclosed in G. Castellani, et al., Frontiers in Genetics Vol 5, pg 1-12 (2014).

In some embodiments, the electrical signal data representative of brain activity of a particular individual is recorded with a sufficiently large sampling rate above 250 and a dynamic range configured to detect sufficient cortical activity in the desired location of the brain. For example, a larger dynamic range is expected to detect more cortical activity than a smaller dynamic range. In one embodiment, the dynamic range is 15 bit resolution of the analog-to-digital (A/D) and above.

In some embodiments, the particular individual is performing a specific cognitive task.

In some embodiments, the specific cognitive task is selected from the group including short and/or long term memory recall, e-learning, meditation, and concentration.

In one embodiment, the particular individual has a particular brain state at a certain time.

Processing the Recorded Electrical Signal Data Representative of Brain Activity of a Particular Individual According the Method of Some Embodiments of the Present Invention Deconstructing the recorded electrical signal data representative of brain activity of a particular individual: In some embodiments, the recorded electrical signal data representative of brain activity of a particular individual is recorded in real-time over a certain time period. In some embodiments, the electrical signal data representative of brain activity of a particular individual is recorded for up to one hour. In some embodiments, the electrical signal data representative of brain activity of a particular individual is recorded for up to 50 minutes. In some embodiments, the electrical signal data representative of brain activity of a particular individual is recorded for up to 40 minutes. In some embodiments, the electrical signal data representative of brain activity of a particular individual is recorded for up to 30 minutes. In some embodiments, the electrical signal data representative of brain activity of a particular individual is recorded for up to 20 minutes. In some embodiments, the electrical signal data representative of brain activity of a particular individual is recorded for up to 10 minutes.

In some embodiments, the real-time recorded electrical signal data representative of brain activity of a particular individual is deconstructed into a plurality of pre-determined deconstructed wavelet packet atoms, utilizing a pre-determined representative set of wavelet packet atoms. Each individual pre-determined deconstructed wavelet packet atom within the plurality of pre-determined deconstructed wavelet packet atoms corresponds to a brain activity feature ("BAF").

In some embodiments, the a pre-determined representative set of wavelet packet atoms is created from a pre determined mother wavelet, selected from an wavelet family selected from the group including, but not limited to: Haar, Coiflet Daubehies, and Mayer wavelet families. Other wavelet families suitable for mother wavelets according to some embodiments of the present invention are described in the web site located at http://www.mathworks.com/help/wavelet/ref/waveletfamilies.html?refresh=true.

In some embodiments, recorded electrical signal data representative of brain activity of a particular individual is deconstructed into a plurality of pre-determined deconstructed wavelet packet atoms, utilizing a pre-determined representative set of wavelet packet atoms according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition based on Shannon equation as detailed in section III. Entropy of a vector.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Intrator, N, Neural Computation 5, 443-455 (1993), whose such specific disclosure is incorporated herein by reference.

In some embodiments, recorded electrical signal data representative of brain activity of a particular individual is deconstructed into a plurality of pre-determined deconstructed wavelet packet atoms, utilizing a pre-determined representative set of wavelet packet atoms according to a combination of the Shannon Entropy and another suitable Best Basis algorithm disclosed in Intrator, N, Neural Computation 4, 98-1-7 (1992), whose such specific disclosure is incorporated herein by reference.

Re-ordering the plurality of pre-determined deconstructed wavelet packet atoms: In some embodiments, the plurality of pre-determined wavelet packet atoms is reordered, according to a pre-determined order. In some embodiments, the re-ordered plurality of pre-determined wavelet packet atoms, is normalized, utilizing a pre-determined normalization factor. In some embodiments, the plurality of pre-determined wavelet packet atoms is only normalized.

In some embodiments, utilizing electrical data recorded via standard EEG recording electrodes, the exemplary specifically programmed processor of the present invention is programmed to first normalize each wavelet packet atom, outputted by at least one band-pass filter, separately based on a dataset of collected data from multiple individuals to determine the distribution of the representation values for each of the wavelet packet atoms separately. In some embodiments, the at least one band-pass filter has 2-36 channels. In some embodiments, the at least one band-pass filter has at least 12 channels. In some embodiments, the at least one band-pass filter has at least 16 channels. In some embodiments, the at least one band-pass filter has at least 32 channels.

The Visual Indication of at Least One Personalized Mental State of the Particular Individual: In some embodiments, the normalized, re-ordered plurality of a statistical measure of projections onto pre-determined wavelet packet atoms is assembled into a visual representation, wherein each individual normalized pre-determined wavelet packet atom in the plurality, corresponds to a BAF, and is arranged in the representation according the pre-determined order. As used herein, a "BAFs representation" refers to a visual representation of the normalized, re-ordered plurality of pre-determined projections onto wavelet packet atoms. An example of a BAFs representation of a subject according to some embodiments of the present invention is shown in FIG. 2.

In some embodiments, the BAFs representation of the particular individual has 121 individual BAFs. Alternatively, in some embodiments, the BAFs representation of the particular individual has up to 200 individual BAFs. Alternatively, in some embodiments, the BAFs representation of the particular individual has from 10 to 200 individual BAFs. Alternatively, in some embodiments, the BAFs representation of the particular individual has from 1 to 1000 individual BAFs. Alternatively, in some embodiments, the BAFs representation of the particular individual has from 30 to 1000 individual BAFs. Alternatively, in some embodiments, the BAFs representation of the particular individual has at least 30 individual BAFs. Alternatively, in some embodiments, the BAFs representation of the particular individual has a number of individual BAFs which is a multiple (e.g., 2×, 3×, 4×, 5×, 6×, etc.) of a number BAFs being recorded.

In some embodiments, the BAFs representation of the subject has 121 individual BAFs. Alternatively, in some embodiments, the BAFs representation of the subject over 200 individual BAFs. Alternatively, in some embodiments, the BAFs representation of the subject has from 10 to 200 individual BAFs. Alternatively, in some embodiments, the BAFs representation of the subject has from 1 to 1000 individual BAFs. Alternatively, in some embodiments, the BAFs representation of the subject has from 30 to 1000 individual BAFs. Alternatively, in some embodiments, the BAFs representation of the subject has at least 30 individual BAFs. Alternatively, in some embodiments, the BAFs representation of the subject has a number of individual BAFs which is a multiple (e.g., 2×, 3×, 4×, 5×, 6×, etc.) of a number of neural networks being analyzed. In some embodiments, the BAFs include traditional EEG recordings.

Figure 2:
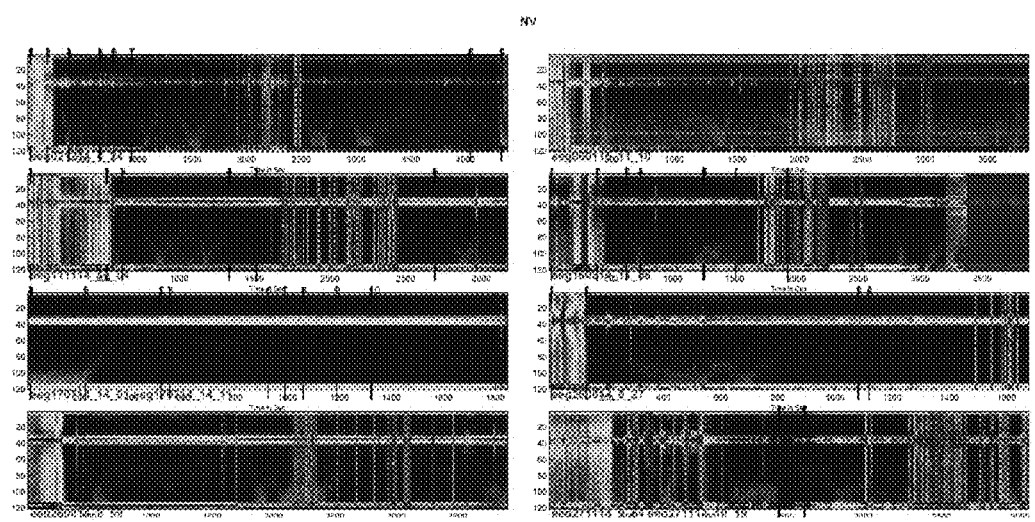
FIG. 2 shows a screenshot of an example of a representation of recording for a brain activity feature of a subject according to some embodiments of the present invention.

Referring to FIG. 2 as an example, each line perpendicular to the y axis represents an activity of a projection onto a single pre-determined wavelet packet atom, (also referred to herein as a BAF). For example, the activity can be represented via at least one suitable statistical measurement of a projection onto a single wavelet packet atom or a group of wavelet packet atoms, where the suitable statistical measurement can be, but not limited to, mean, standard deviation, and the like. In some embodiments, the BAFs representation can be color coded. For example, as shown in FIG. 2, various activity area(s) on an intensity spectrum can be presented, for example but not limited to, by presenting high activity area(s) as more darkly shaded regions of at least one particular color ("hot") to low activity tends area(s) as more lighted shaded region(s) of the at least one color or at least one other color ("cold"), and any continuous shading in between based on corresponding activity level. Each column perpendicular to the x axis represents a vector of brain activity state (the BAFs representation) at a specific time or specific time period. Thus, the x axis is measured in time (e.g., milliseconds, seconds, minutes, hours, days, etc.). In some embodiments, the image is normalized by a suitable non-linear transformation such as, for example, histogram equalization, prior to the color coding each brain activity (BAF) of the plurality of BAFs.

In some embodiments, the exemplary specifically programmed processor of the present invention is programmed to cluster the electrical signal data representative of brain activity of a particular individual before a pre-determined predictor is determined. For example, the exemplary specifically programmed processor of the present invention is programmed to generate a collection of m-dimensional vectors from projections on m pre-determined deconstructed wavelet packet atoms which can be further clustered into different brain states. In some embodiments, the exemplary specifically programmed processor of the present invention is programmed to determine a number of brain states by using at least one machine learning technique. For example, the exemplary specifically programmed processor of the present invention is programmed to utilize hierarchical clustering to analyze the clustered data and to decide which clusters to group together based on the relative distance between their members.

In some embodiments, the exemplary specifically programmed processor of the present invention is programmed to utilize the cluster membership construct the plurality of pre-determined predictors based, at least in part, on:

1) the distance from a cluster center or from different members of the cluster, and/or
2) a sequence of cluster membership that preceded the current frame.

For example, the exemplary specifically programmed processor of the present invention is programmed to utilize at least one temporal model (e.g., but not limited to, a Markov chain, a hidden Markov model, other similarly suitable models) based on the cluster membership to determine a particular predictor of the library of predictors.

In some embodiments, after the cluster membership is assigned to each window frame, the exemplary specifically programmed processor of the present invention is programmed to generate at least one temporal structure probabilistic model. For example, in text analysis, from the data, the exemplary specifically programmed processor of the present invention is programmed to: construct the vocabulary of letters (specific clusters); identify words based on segmentation of letters, construct the words vocabulary from the identified words, and, interpret particular grammatical rules to create sentences from the words. For example, the first step is to construct a matrix of probability to move from one letter to the other.

Identification of an Underlying Mental State, an Underlying Neurological Condition, or a Combination of an Underlying Mental State and Neurological Condition According the Method of Some Embodiments of the Present Invention In some embodiments, the visual indication of at least one personalized mental state of the particular individual is used to identify an underlying mental state, an underlying neurological condition, or a combination of an underlying mental state and an underlying neurological condition, in the particular individual, wherein the specifically programmed computer utilizes at least one machine learning algorithm selected from the group consisting of logistic regression modeling, support vector machine modeling, and a deep learning modeling, to assign at least one specific brain state to the visual indication of at least one personalized mental state of the particular individual, wherein the at least one specific brain state is associated with a mental state, a neurological condition, or a combination of a mental state and a neurological condition.

In some embodiments, the exemplary specifically programmed processor of the present invention is programmed to identify an underlying mental state, an underlying neurological condition, or a combination of an underlying mental state and an underlying neurological condition, in the particular individual utilizing at least one machine learning algorithm such as, but not limited to, logistic regression modeling, support vector machine modeling, and a deep learning modeling. Specifically, in some embodiments, the exemplary specifically programmed processor of the present invention is programmed to execute at least the following steps:

1) separating the electrical signal data representative of brain activity of a particular individual into training, validation and test data sets;
2) generating a family of models based on the training set, optimized on the validation set;
3) testing the performance of each model on the test set;
4) repeating steps 1-3 for different parameters of a particular AI model (e.g. the regularization parameter in a ridge regression model; the number of hidden units in a feed forward neural network; the weight decay parameter in a feed forward neural network; types and a number of kernels in a kernel model such as support vector machine; a combination of Gaussians and the regularization parameters in a support vector machine; a combination of Gaussians models; etc.); and 5) after a set of model parameters is determined, obtaining prediction results on a new data set and repeat the steps 1-4 for different families of orthogonal decomposition and other model parameters obtained from the recorded electrical signal data representative of brain activity of a particular individual.

In some embodiments, electrical signal data representative of brain activity of a particular individual is recorded when the particular individual has a particular mental state. In some embodiments, the particular mental state is unknown, and the methods according to some embodiments of the present invention are utilized to identify the particular mental state.

Examples of the particular mental state include, but are not limited to, seizure, fear, anxiety, pain, sleep states (e.g. REM sleep), awake, alert, fatigue, anaesthetized, meditation states, stress, other moods, different brain states associated with dementia, a lack of response, or inappropriate response to external stimuli associated with autism, or autism spectrum disorder, and the like. An example of a BAFs representation of a subject having a particular mental state is shown in FIG. 3.

Figure 3A:
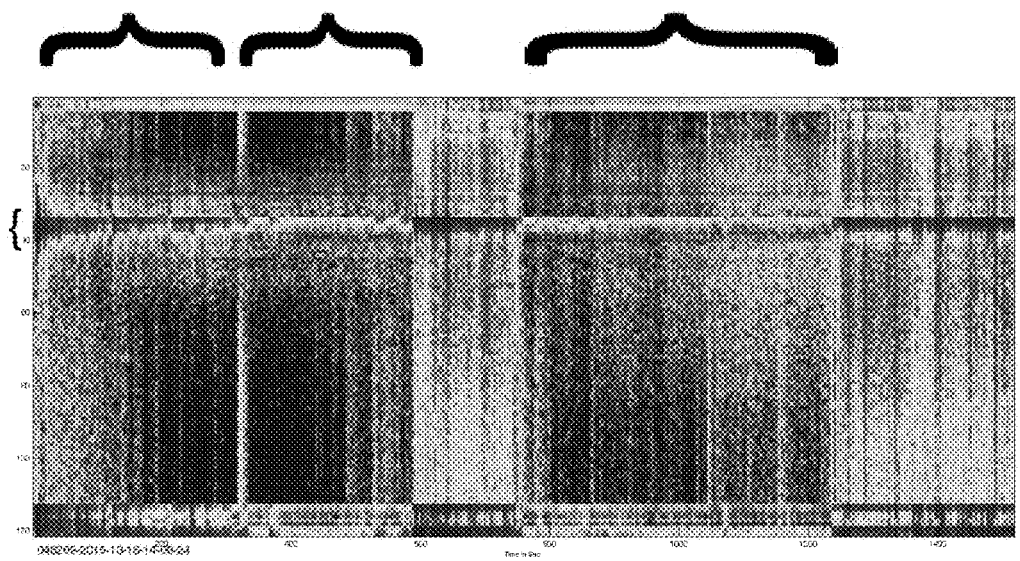
Figure 3A:
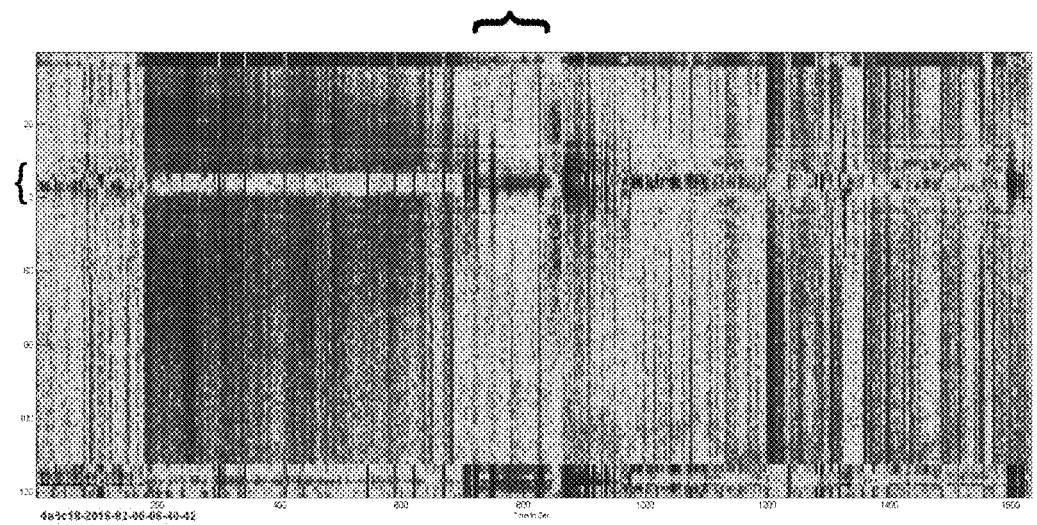

Referring to FIG. 3A, shows the brain activity representation of an experienced yogi that is performing three types of meditation (indicated via the horizontal brackets). After the first two meditations and after the third meditation, the yogi explains what he is doing. A range in BAFs is indicated with the vertical brackets. This collection of BAFs is associated with awareness. It is clear that one meditation emphasizes only these awareness channels, and it is evident in the activity when the yogi explains what meditation he is doing.

Referring to FIG. 3B, a BAFs representation is shown from an individual in a vegetative state. The BAFs highlights in FIG. 3A are shown, and are not active. However, administration of a medical brain stimulation to the individual was able to activate the BAFs associated with awareness for a short period of time. This provides an example to the ability to determine the effect of medications with the BAF representation.

In some embodiments, the electrical signal data representative of brain activity of a particular individual is recorded when the particular individual is performing a specific cognitive task. In some embodiments, the methods according to some embodiments of the present invention identify an underlying mental state, an underlying neurological condition, or a combination of an underlying mental state and an underlying neurological condition, based, at least in part, on the electrical signal data representative of brain activity of a particular individual recorded while the particular individual is performing the specific cognitive task.

Examples of the specific cognitive task include, but are not limited to, short and long term memory recall, identification of stimuli, meditation, learning, watching a movie, observing images, intense concentration during motor operation, response to a sensory stimulus, and the like. An example of a BAFs representation of a subject performing a specific cognitive task is shown in FIG. [6].

In some embodiments, the sensory stimulus can be auditory, tactile, olfactory, visual, and the like.

In some embodiments, the assignment of at least one specific brain state to the visual indication of at least one personalized mental state of the particular individual identifies an abnormality in at least one neural network in the brain of the particular individual associated with a particular neurological condition.

In some embodiments, the abnormality in at least one neural network in the brain of the particular individual is used to diagnose the particular individual having a neurological condition.

Figure 4:
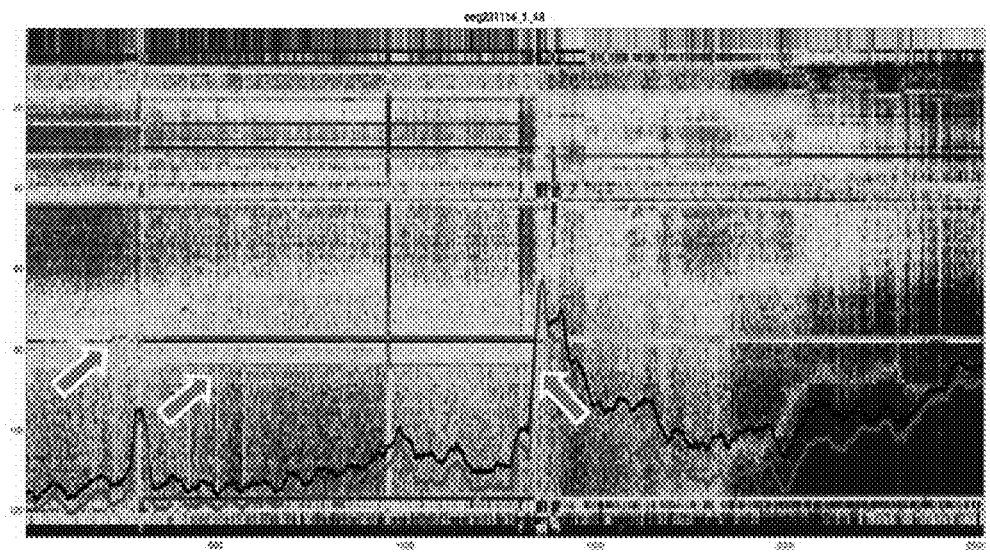
FIG. 4 shows a screenshot of an example of a brain activity features (BAFs) representation of a subject according to some embodiments of the present invention.

In some embodiments, the neurological condition is selected from the group consisting of, Alzheimer's disease, dementia, stress, fatigue, anxiety, epilepsy, traumatic brain injury, loss of cognitive function, coma, a lack of response, or inappropriate response to external stimuli associated with autism, or autism spectrum disorders, a lack of concentration, and sleep disorders. An example of a BAFs representation of a subject with a neurological condition is shown in FIG. 4.

In some embodiments, the particular individual's neurological condition is unknown, and the methods according to some embodiments of the present invention identify the neurological condition.

In some embodiments, the at least one specific brain state is used to determine the emotional state of the particular individual.

In some embodiments, the particular individual is receiving a therapy, and the visual indication of at least one personalized mental state of the particular individual is used to determine the effectiveness of the therapy.

For example, by way of illustration, early intervention in autism patients, at around 6 months of age can improve the treatment of autism. In another example, an earlier detection of abnormal activity in at least one neuronal network that is associated with epilepsy in the brain of an individual can improve the treatment of epilepsy, or warn the individual, or the individual's care giver that a seizure is occurring, or will occur. In another example, an earlier detection of abnormal activity in at least one neuronal network that is associated with migraine in the brain of an individual can improve the treatment of migraine, or warn the individual, or the individual's care giver that a migraine is occurring, or will occur. In another example, an earlier detection of abnormal activity in at least one neuronal network that is associated with an ischemic event in the brain of an individual can improve the treatment of ischemic injury, or warn the individual, or the individual's care giver that an ischemic event, such as, for example, a transient ischemic event, or stroke is occurring, will occur, or has occurred. In some embodiments, the brain activity of the particular individual may be recorded whilst the subject is asleep, which, in the case of certain ischemic conditions, is when such conditions are more likely to occur.

In some embodiments, the particular individual is receiving a therapy, and the visual indication of at least one personalized mental state of the particular individual is used to determine the nature of the therapy to be administered.

In some embodiments, the particular individual is receiving a therapy, and the visual indication of at least one personalized mental state of the particular individual is used to determine the duration of the therapy.

In some embodiments, the particular individual is receiving a therapy, and the visual indication of at least one personalized mental state of the particular individual is used to determine the dosing regimen of the therapy.

In some embodiments, the therapy is an anesthetic agent, and the effectiveness of the anesthetic is determined by the particular individual's ability to feel pain and/or the individual's perceived pain level and the correlation to the change in the visual indication of at least one personalized mental state of the particular individual.

In some embodiments, the therapy is a migraine therapy, and the effectiveness of the migraine therapy is determined by the particular individual's ability to feel pain, and/or the individual's perceived pain level and the correlation to the change in the visual indication of at least one personalized mental state of the particular individual.

In some embodiments, the migraine therapy is a medication. Alternatively, in some embodiments, the migraine therapy is guided imagination. Alternatively, in some embodiments, the migraine therapy is hypnosis. Alternatively, in some embodiments, the migraine therapy is meditation.

In some embodiments, in contrast to the analysis of fetal brain activity using Amplitude Integrated EEG which typically detects the two brain conditions of sleep and awake states, and the dynamics of shift from one state to the other to identify the degree of brain damage, the exemplary specifically programmed processor of the present invention is programmed to perform group analysis on a group of brain states of infants, and determine the brain states of the infant at a certain time.

In another example, in neural marketing, in some embodiments, the exemplary specifically programmed processor of the present invention is programmed to perform group analysis on a group of brain states in individuals receiving a stimulation at each time frame, and to determine the proportions in the group that are in the same brain state at a given window frame. This enables to measure the engagement of the group with the stimulation, as when a larger portion of the group is found in the same brain state, it is likely that this happens due to the stimulation, thus the group is considered to be engaged and reacting to the stimuli. The specific brain state, at which a portion of the group is in, can correspond to the specific reaction to the stimuli, allowing for feedback training.

In some embodiments, the methods of the present invention determine a mental state of a particular individual at a first time point. In some embodiments, brain of the particular individual changes from one mental state to another, but remains in a first mental state for the majority of the time. In some embodiments, the first mental state is not favorable. In some embodiments, the system may supply a stimulus that encourages the brain of the particular individual to enter a second, more favorable mental state, via neural feedback. For example, by way of illustration, the particular individual may be in a coma, and the first mental state may be a state of non-responsiveness. The system may supply a stimulus that encourages the brain of the particular individual to enter a second, more responsive mental state.

In another example, the patient may have an autism spectrum disorder, and the first mental state may be the individual refusing, or being unable to maintain eye contact with another person. The system may supply a stimulus that encourages the brain of the particular individual to enter a second mental state where the individual is more easily capable of maintaining eye contact.

The Plurality of Pre-Determined Predictors

In some embodiments, an individual pre-determined predictor associated with a particular brain state within the plurality of pre-determined predictors is generated by the steps including:
  i. obtaining the pre-determined representative set of wavelet packet atoms by:
    a. obtaining from a plurality of individuals, by the specifically programmed processor, at least one plurality of electrical signal data representative of a brain activity of a particular brain state;
    b. selecting a mother wavelet from a plurality of mother wavelets,
      wherein mother wavelet is selected from an wavelet family selected from the group consisting of: Haar, Coiflet Daubehies, and Mayer wavelet families;
    c. causing, by the specifically programmed processor, the at least one plurality of electrical signal data to be deconstructed into a plurality of wavelet packet atoms;
    d. storing the plurality of wavelet packet atoms in at least one computer data object;
    e. determining, an optimal set of wavelet packet atoms, and storing the optimal set of wavelet packet atoms in at least one computer data object,
      wherein the determining is via utilizing a Best Basis algorithm; and
    f. applying, by the specifically programmed processor, wavelet denoising to the number of wavelet packet atoms in the optimal set;
  ii. obtaining the pre-determined ordering of wavelet packet atoms by:
    a. projecting, by the specifically programmed processor, the at least one plurality of electrical signal data representative of a brain activity for each 4 second window of the data onto the pre-determined representative set of wavelet packet atoms;
    b. storing the projections in at least one computer data object;
    c. determining, by the specifically programmed processor, the wire length for every data point in the projection by determining the mean absolute distance of the statistical measure of the projections of different channels from their adjacent channels;
    d. storing the wire length data in at least one computer data object; and
    e. optionally re-ordering the stored projections, by the specifically programmed computer to minimize a statistical value of the wire length value across each time window, and across all individuals within the plurality of individuals, and across the projections; and;
  iii. obtaining the pre-determined set of normalization factors by:
    a. determining, by the specifically programmed computer, the mean and standard deviation of the values of the stored projections.

To generate a library of a plurality of pre-determined predictors requires an illustrative library of at least one plurality of electrical signal data representative of a brain activity of a particular brain state. Generation of an illustrative library of at least one plurality of electrical signal data representative of a brain activity of a particular brain state requires obtaining a sufficient collection of electrical signal data representative of a brain activity of a particular brain state (e.g., 100 recordings; 1,000 recording; 10,000 recordings; 100,000 recordings; 1,000,000 recordings, etc.) In general, a recording of 3000 seconds of each event, is sufficient for a robust detection of that brain state event. The larger the number of observations, the more robust the detection is. The electrical signal data representative of a brain activity of a particular brain state can be from a sufficient number of individuals (e.g., 100; 1,000; 10,000; 100,000; 1,000,000, etc.) and be recorded during various (e.g., different in kind, different in intensity, etc.) activities, cognitive tasks and neurological conditions, leading to a variety of brain states.

In some embodiments, the library of a plurality of predetermined predictors can be tailored to one or more specific goals. For example, if there is a need to emphasize on detection of a specific brain activity event, for example, detection of abnormalities which exist at a certain cortical location occurring before an epileptic seizure occurs, or at an early stage of migraine, then more emphasis should be put on recording during such times. Such emphasis is given by recording from a single subject at times when such event occurs, or recording from multiple subjects at those times. Another example may be recording from subjects that are performing an attention test such as T.O.V.A. test (The TOVA Company, Los Alamitos, Calif.). Then a recording of a number of subjects performing the same task is obtained, rather than recording from a number of subjects that exhibit a certain brain abnormality such as a certain type of epilepsy. In another example, based on the goal, in some embodiments, a plurality of subjects can be asked to perform a specific cognitive task. Examples of the specific cognitive task include, but are not limited to, memory recall, identification of stimuli, performing an attention task, meditation, learning, watching a movie, observing images, intense concentration during motor operation, and the like.

Deconstructing the at least one plurality of electrical signal data: In some embodiments, the at least one plurality of electrical signal data is recorded over a certain time period. In some embodiments, the at least one plurality of electrical signal data is recorded for up to one hour. In some embodiments, the at least one plurality of electrical signal data is recorded for up to 50 minutes. In some embodiments, the at least one plurality of electrical signal data is recorded for up to 40 minutes. In some embodiments, the at least one plurality of electrical signal data is recorded for up to 30 minutes. In some embodiments, the at least one plurality of electrical signal data is recorded for up to 20 minutes. In some embodiments, the at least one plurality of electrical signal data is recorded for up to 10 minutes.

In some embodiments, the recorded at least one plurality of electrical signal data is deconstructed into a plurality of deconstructed wavelet packet atoms. Each individual deconstructed wavelet packet atom within the plurality of deconstructed wavelet packet atoms corresponds to a brain activity feature ("BAF").

In some embodiments, the exemplary specifically programmed processor of the present invention is programmed deconstruct the at least one plurality of electrical signal data into a plurality of deconstructed wavelet packet atoms, with different mother wavelets, and other orthogonal decompositions such as but not limited to, orthogonal cosine transform and wavelet transform. In some embodiments, the exemplary specifically programmed processor of the present invention is programmed to utilize a particular orthogonal decomposition to minimize the decomposition processing time which is proportional to n log(n) time where n is the number of samples in a window frame.

In some embodiments, the mother wavelet is selected from an wavelet family selected from the group including, but not limited to: Haar, Coiflet Daubehies, and Mayer wavelet families. Other wavelet families suitable for mother wavelets according to some embodiments of the present invention are described in the web site located at http://www.mathworks.com/help/wavelet/ref/waveletfamilies.html?refresh=true.

In some embodiments, the exemplary specifically programmed processor of the present invention is programmed to obtained, based on the orthogonal decomposition algorithm, a collection of n dimensional vectors, where each vector represents one BAF.

In some embodiments, the exemplary specifically programmed processor of the present invention is programmed to perform the decomposition to achieve at least one pre-determined goal. For example, the at least one pre-determined goal can be based on identifying a common Best Basis which achieves a particular discrimination at a particular coefficient distribution (an unsupervised/supervised hybrid goal) and which can be commonly utilized for the data analysis with respect to a group of individuals.

In some embodiments, the exemplary specifically programmed processor of the present invention is programmed to determine projections (convolutions) onto the chosen basis functions or some statistics of these projections to generate output interpretive of particular brain activity(ies) associated with particular BAF(s). For example, the exemplary specifically programmed processor of the present invention is programmed to determine particular BAF(s) based on an activity in each such projection. In some embodiments, the exemplary specifically programmed processor of the present invention is programmed to estimate the energy of each projection (e.g., the variance of the signal), a maximal value or other suitable statistical measurement of the orthogonal distribution, such as, but not limited to, a value of the negative entropy.

In some embodiments, the recorded at least one plurality of electrical signal data is deconstructed into a plurality of deconstructed wavelet packet atoms, according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition based on Shannon equation as detailed in section III. Entropy of a vector.

Specifically, the exemplary specifically programmed processor of the present invention identifies a smallest-entropy basis to be utilized in orthogonal decomposition of a particular at least one plurality of electrical signal data. In some embodiments, the exemplary specifically programmed processor of the present invention performs the Shannon entropy analysis on an at least one plurality of electrical signal data to obtain the joint best basis. When considering an at least one plurality of electrical signal data to obtain the joint best basis, the in one embodiment of this patent, it is possible to choose a map M to include additional characteristics which emphasize specific properties of the joint at least one plurality of electrical signal data. For example, if M(1) and M(2) satisfy the definition of the map M being the additive information cost functions, leading to an optimal basis which relies on the sum of both functions. In some embodiments, the exemplary specifically programmed processor of the present invention is programmed to add a new additive cost function which measures a distribution of coefficients at each node in a particular wavelet packet tree to identify the functional M which seeks wavelet packet coefficients with minimal Shannon entropy or with the modified additive optimization function (across the wavelet decomposition) on average across all data observations.

In some embodiments, the recorded at least one plurality of electrical signal data is deconstructed into a plurality of deconstructed wavelet packet atoms, according to another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, the recorded at least one plurality of electrical signal data is deconstructed into a plurality of deconstructed wavelet packet atoms, according to another suitable Best Basis algorithm disclosed in Intrator, N, Neural Computation 5, 443-455 (1993), whose such specific disclosure is incorporated herein by reference.

In some embodiments, the recorded at least one plurality of electrical signal data is deconstructed into a plurality of deconstructed wavelet packet atoms, according to another suitable Best Basis algorithm disclosed in Intrator, N, Neural Computation 4, 98-1-7 (1992), whose such specific disclosure is incorporated herein by reference.

For example, in some embodiments, the exemplary specifically programmed processor of the present invention is programmed to utilize a moving window frame along the time series to obtain different data observations result. In one example, the exemplary specifically programmed processor of the present invention is programmed to utilize a particular window frame and an overlap for the analysis of data segments. In one example, the exemplary specifically programmed processor of the present invention is programmed to utilize a window frame of 4 seconds with an overlap of 75% between consecutive window frames. In some embodiments, the exemplary specifically programmed processor of the present invention is programmed to utilize the window which has a length that is an exponent of 2, so, for example, if sampling rate is 256 Hz, a 4 second window would result in 1024 samples. In another example, if the sampling frequency of 250 Hz, the exemplary specifically programmed processor of the present invention is programmed to utilize the window frame that is a slightly above 4 seconds (e.g., 4.05-4.2). In another example, if the sampling frequency of 496 Hz, the exemplary specifically programmed processor of the present invention is programmed to utilize the window frame that is a slightly above 4 seconds (e.g., 4.05-4.2). In another example, if the sampling frequency of 496 Hz, the exemplary specifically programmed processor of the present invention is programmed to utilize the window frame that is a slightly above 4 seconds (e.g., 4.05-4.2).

In another example, the exemplary specifically programmed processor of the present invention is programmed to utilize a window frame which progresses by 1 second between adjacent frames to obtain vector updates every one second, thus generating a projections matrix of size 121×N (the number of seconds in the data)−3 (due to the first frame of 4 seconds and then each frame progresses by 1 second). In some embodiments, the exemplary specifically programmed processor of the present invention is programmed to rescaling the full matrix to obtain the maximal dynamic range of the visual map of the data.

Determination of the optimal set: In some embodiments, the optimal set of wavelet packet atoms is determined according to the Best Basis algorithm disclosed in Coifman, R. R., & Wickerhauser, M. V., IEEE Transactions on Information Theory, 38(2), 713-718 (1992), which is incorporated herein by reference, specifically the description of orthogonal decomposition In some embodiments, the optimal set of wavelet packet atoms is determined according to another suitable Best Basis algorithm disclosed in Stainvas, I and Intrator, N., In. J. Appl. Mathematics and Statistics, 4(J06), 1-22 (2006), whose such specific disclosure is incorporated herein by reference.

In some embodiments, the optimal set of wavelet packet atoms is determined according to another suitable Best Basis algorithm disclosed in Intrator, N, Neural Computation 5, 443-455 (1993), whose such specific disclosure is incorporated herein by reference.

In some embodiments, the optimal set of wavelet packet atoms is determined according to another suitable Best Basis algorithm disclosed in Intrator, N, Neural Computation 4, 98-1-7 (1992), whose such specific disclosure is incorporated herein by reference.

In some embodiments, the number of wavelet packet atoms in the optimal set is reduced by application of the wavelet denoising algorithm disclosed in Donoho D. L., IEEE Transactions on Information Theory, 41(3), 613-627 (1995).

In some embodiments, the number of wavelet packet atoms in the optimal set is reduced by application of an L1 denoising method.

some embodiments, the number of wavelet packet atoms in the optimal set is reduced by application of an L2 denoising method.

some embodiments, the number of wavelet packet atoms in the optimal set is reduced by application of a hard threshold method.

Re-ordering the plurality of deconstructed wavelet packet atoms: In some embodiments, the denoised optimal set of wavelet packet atoms is reordered, so that more physiologically correlated BAFs, based on analysis of the total signal data, are visually presented to be geographically/spatially closer, as, for example shown in FIG. 5.

In some embodiments, the reordering is optional.

In some embodiments, the denoised optimal set of wavelet packet atoms is reordered by the specifically programmed computer performing the steps consisting of:
1. determining the wire length for every data point in the projection by determining either the mean or sum of absolute distance of the statistical measure of the projections of different channels from their adjacent channels;
2. storing the wire length data in at least one computer data object; and
3. re-ordering the stored projections to minimize a value of wither the mean or sum of the wire lengths across the projections, across each 4 second window, and across all individuals within the plurality of individuals.

In some embodiments, the statistical value for the re-ordering is selected from the group consisting of: the mean of the sum of the absolute differences of the wavelet packet atoms, and a mean of the sum of (1−correlation) of the wavelet packet atoms.

Obtaining the pre-determined set of normalization factors: In some embodiments, the set of pre-determined set of normalization factors is obtained by determining the mean and standard deviation of the values of the stored projections.

In some embodiments, the brain activity is represented by the energy of the individual BAF. In some embodiments, the energy is determined based on the variance of the signal. In some embodiments, the energy is the maximal value of the energy of the individual BAF. In some embodiments, the energy is the negative entropy of the energy coefficients of the individual BAF as is Coifman and Wickerhauser.

In some embodiments, the BAFs representation of the subject is used to determine the contribution of each BAF to the total energy of the signal being recorded. For example, the BAFs representation of the subject is used to determine the contribution of each BAF to the total energy of the signal being recorded based, at least in part, on:

1) at least one orthogonal condition utilized for the orthogonal decomposition and/or
2) a summation of orthogonal components utilizing the Parseval's equality which holds for the BAFs representation.

In some embodiments, the BAFs representation of the subject is used to obtain the contribution of each BAF to the total length of a virtual wire that is created from obtaining a wire segmentation of the peaks of BAFs; where the virtual wire identifies at least one communication passage being utilized by isolated brain subsystems of the subject to communicate with each other. In some embodiments, the contribution of each BAF to the total length of the virtual wire measures the smoothness of the brain activity in a different, geographically close BAF.

In some embodiments, the contribution of each BAF to the total energy of the signal and the contribution of each BAF to the total length of each virtual wire that is created from obtaining a wire segmentation of the peaks of BAF activity is used to determine which BAF is being presented in the final BAFs representation. In some embodiments, specific BAFs, which are presented in the BAFs representation of the subject, are those BAFs whose contribution to the variance is suitably high and if their contribution to the total virtual wire length is low.

In some embodiments, the present invention provides a system that is capable of an underlying mental state, an underlying neurological condition, or a combination of an underlying mental state and an underlying neurological condition, in the particular individual. In some embodiments, therefore, the system may be used by a physician.

In some embodiments, the apparatus used to record the electrical activity of the brain of a subject may be worn continuously, and is non-invasive, or unobtrusive. Thus, in some embodiments, the identification of the neurological impairment, or determination of the subject's first mental state may be achieved at an earlier time, or may be achieved more efficiently than other methods, because the subject is monitored in a more natural, or less clinical setting. In some embodiments, the system of the present invention enables an earlier detection, identification, or diagnosis of an individual's mental state and/or neurological condition.

In some embodiments, the present invention provides a specifically programmed computer system including:
a. at least one specialized computer machine comprising:
   i. a non-transient memory, electronically storing particular computer executable program code; and
   ii. at least one computer processor which, when executing the particular program code, becomes a specifically programmed computer processor configured to perform at least the following operations:
      1. obtaining, in real-time, by a specifically programmed processor, electrical signal data representative of brain activity of a particular individual;
      2. processing, in real-time the electrical signal data representative of brain activity of a particular individual based upon an individual pre-determined predictor associated with a particular brain state, selected from a library of predictors containing a plurality of pre-determined predictors, wherein each individual pre-determined predictor is associated with a unique brain state,
      wherein the pre-determined predictor associated with a particular brain state comprises:
         i. a pre-determined mother wavelet,
         ii. a pre-determined representative set of wavelet packet atoms,
         iii. a pre-determined ordering of wavelet packet atoms, created from the pre-determined mother wavelet, and
         iv. a pre-determined set of normalization factors,
      wherein the processing comprises:
         i. causing, by the specifically programmed processor, the electrical signal data to be deconstructed into a plurality of pre-determined deconstructed wavelet packet atoms, utilizing the pre-determined representative set of wavelet packet atoms,
         wherein time windows of the electrical signal data are projected onto the pre-determined representative set of wavelet packet atoms
            wherein the projection is via convolution or inner product, and
         wherein each pre-determined representative wavelet packet atom corresponds to a particular pre-determined brain activity feature from a library of a plurality of pre-determined brain activity features;
         ii. storing the plurality of pre-determined deconstructed wavelet packet atoms in at least one computer data object;
         iii. causing, by the specifically programmed processor, the stored plurality of pre-determined deconstructed wavelet packet atoms to be re-ordered within the computer data object, based on utilizing a pre-determined order;
         iv. obtaining a statistical measure of the activity of each of the re-ordered plurality of pre-determined deconstructed wavelet packet atoms; and
         v. normalizing the re-ordered plurality of pre-determined wavelet packet atoms, based on utilizing a pre-determined normalization factor; and
      3. outputting, a visual indication of at least one personalized mental state of the particular individual, at least one personalized neurological condition of the particular individual, or both, based on the processing,
      wherein an individual pre-determined predictor associated with a particular brain state within the plurality of pre-determined predictors is generated by the steps consisting of:
         ii. obtaining the pre-determined representative set of wavelet packet atoms by:
            1. obtaining from a plurality of individuals, by the specifically programmed processor, at least one plurality of electrical signal data representative of a brain activity of a particular brain state;
            2. selecting a mother wavelet from a plurality of mother wavelets,
               wherein mother wavelet is selected from an wavelet family selected from the group consisting of: Haar, Coiflet Daubehies, and Mayer wavelet families;
            3. causing, by the specifically programmed processor, the at least one plurality electrical signal data to be deconstructed into a plurality of wavelet packet atoms, using the selected mother wavelet;
            4. storing the plurality of wavelet packet atoms in at least one computer data object;
            5. determining, an optimal set of wavelet packet atoms using the pre-determined mother wavelet, and storing the optimal set of wavelet packet atoms in at least one computer data object, wherein the determining is via utilizing a Best Basis algorithm; and 6. applying, by the specifically programmed processor, wavelet denoising to the number of wavelet packet atoms in the optimal set;

ii. obtaining the pre-determined ordering of wavelet packet atoms by:

1. projecting, by the specifically programmed processor, the at least one plurality of electrical signal data representative of a brain activity for each 4 second window of the data onto the pre-determined representative set of wavelet packet atoms;
2. storing the projections in at least one computer data object;
3. determining, by the specifically programmed processor, the wire length for every data point in the projection by determining the mean absolute distance of the statistical measure of the projections of different channels from their adjacent channels;
4. storing the wire length data in at least one computer data object; and
5. re-ordering the stored projections, by the specifically programmed computer to minimize a statistical value of the wire length value across each time window, and across all individuals within the plurality of individuals, and across the projections; and iii. obtaining the pre-determined set of normalization factors by:

1. determining, by the specifically programmed computer, the mean and standard deviation of the values of the stored projections.

Reference is now made to the following examples, which together with the above descriptions illustrate some embodiments of the invention in a non-limiting fashion.

EXAMPLES

Example 1

Figure 5:
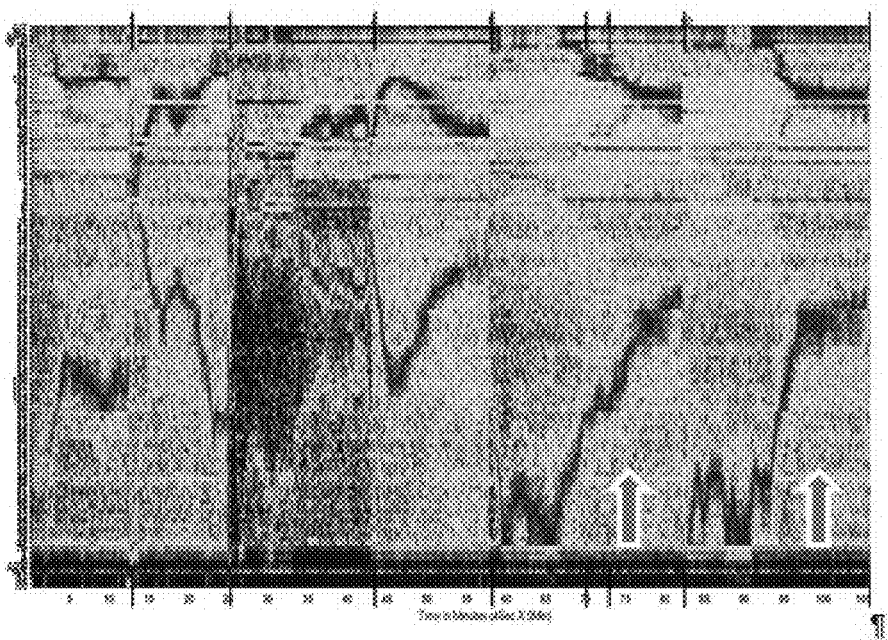
FIG. 5 shows a screenshot of an example of a BAFs representation of a subject according to some embodiments of the present invention.

BAF Representations Obtained from Multiple Subjects Performing Specific Cognitive Tasks FIG. 5 shows a BAF representation from 7 subjects. Each raw (Y axis) represents the activity of a single BAF. The color coding is ("hot") indicating that high activity tends towards red and low activity tends towards blue. Each column (X axis) represents a vector of activity at a specific time frame. Thus, the X axis is measured in time (minutes or seconds). FIG. 5 is measured in minutes. The specific figure represents activity of 6 subjects during a cognitive task. Thus, it is possible to concatenate EEG of different recordings together so that one figure (or matrix of BAF) represents activity of different tasks, or different subjects performing (different) tasks. In this specific figure, the arrows indicate two subjects that have a relatively similar pattern of activity during the task. Thus, this figure represents different cognitive strategies performed during the same cognitive task, performed by different subjects.

Example 2

Figure 6:
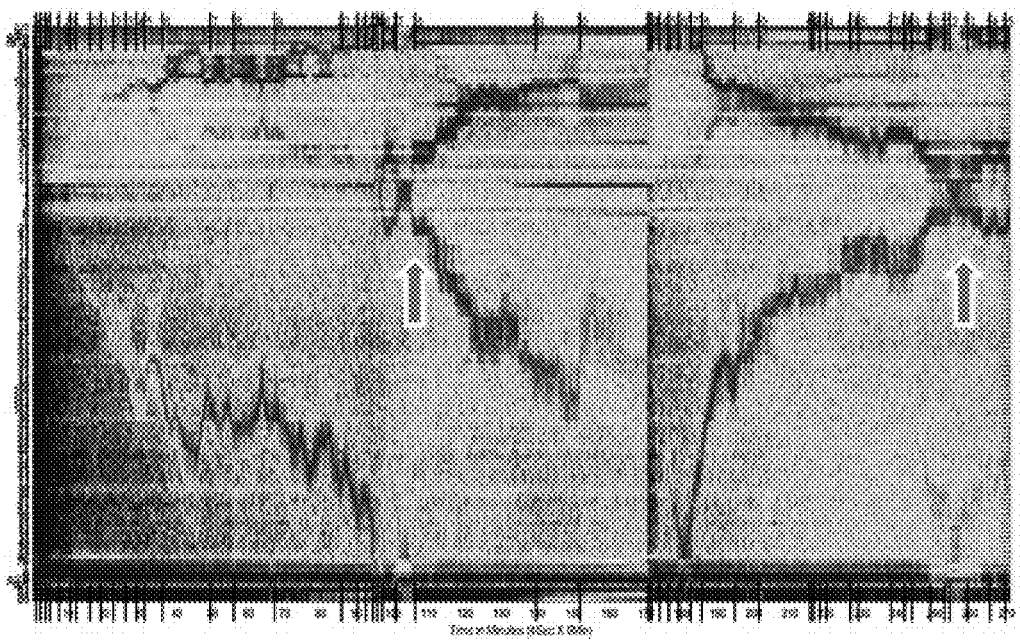
FIG. 6 shows a screenshot of an example of a BAFs representation of a subject according to some embodiments of the present invention.

BAF Representations Obtained from a Subject Watching Three Movies that Elicit Different Emotional Responses Brain activity (BAF) during three movies (each recorded at a different time). Referring to FIG. 6, it can be seen that the activity of the second and third movie is more similar in terms of the BAFs that are active, compared with those active in the first movie. The first movie (Derailed) includes violence and horror, while the other two movies (Stolen Life and Skin) are more associated with sadness and warm feelings. The arrows mark the time of strong positive emotional feelings in the two movies. It is evident that the BAFs active at that time are the same. They are also active in FIG. 7 below during meditation.

Example 3

BAF Representations Obtained from Seven Subjects Performing E-Learning Tasks

Figure 7:
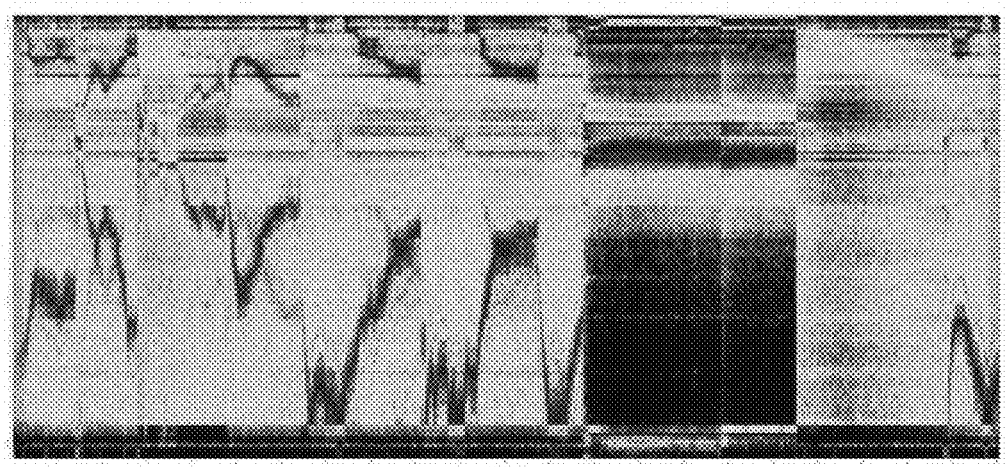
FIG. 7 shows a screenshot of an example of a BAFs representation of a subject according to some embodiments of the present invention.

EEG recordings were obtained from 7 subjects, according to some embodiments of the present invention, whilst the subjects were performing specific e-learning tasks. The BAF representations are shown in FIG. 7. The task included information gathering and then answering questions at two levels of difficulty (this was the same representation from FIG. 5). This was followed by two experienced meditators performing Gayatri Meditation and an inexperienced person performing Japa meditation immediately followed by music listening. The active BAFs during the Gayatri meditation were similar to those that are active during the positive emotional parts in the movies (FIG. 6). There is evidence that experienced meditators demonstrate increased co activation of mPFC, insula, and temporal lobes while reducing the activity of the default mode network. There is also evidence of a sense of happiness.

Example 4

Figure 8:
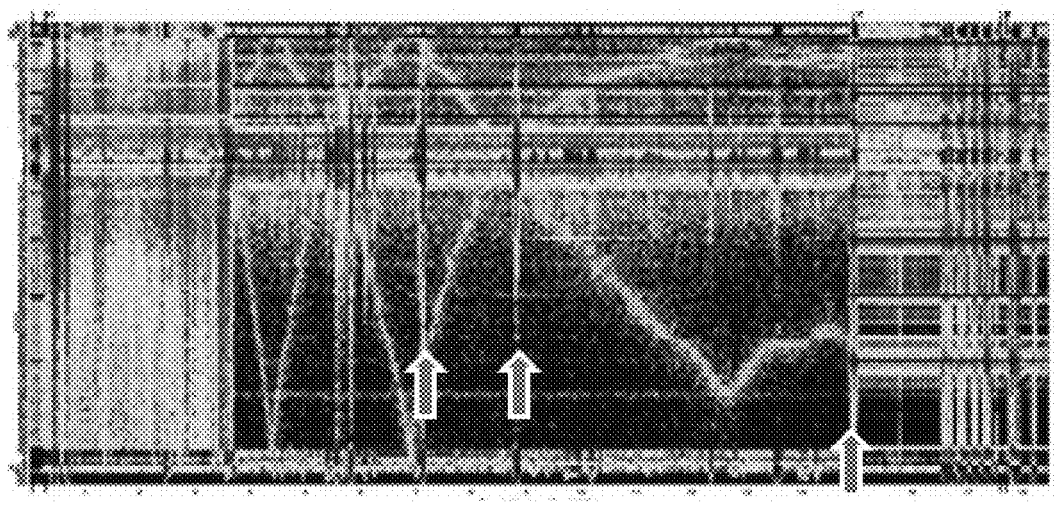
FIG. 8 shows a screenshot of an example of a BAFs representation of a subject according to some embodiments of the present invention.

BAF Representations Obtained from Subject Receiving a Painful Stimulus, Before and After Receiving an Anesthetic Referring to FIG. 8, the figure represents the brain activity after receiving anesthesia. The Anesthesia is induced where the picture becomes mainly blue. It is seen that a region of activity (the same region in BAF space that was active during meditation) remains active. This does not happen to all patients. The two arrows (on the left) indicate time when pain is induced during the surgery. It is clear that there is a reactive brain activity to this induced pain. The arrow on the right represents the beginning of use of a laser surgical tool, which creates a large electric noise, thus, the recording from that point is less clear. One observation in this subject is that once the laser knife starts its action (stronger pain) the activity in the region that was active during meditation stops.

Example 5

BAF Representations Obtained from Subjects During a Sleep-Wake Cycle

Figure 9:
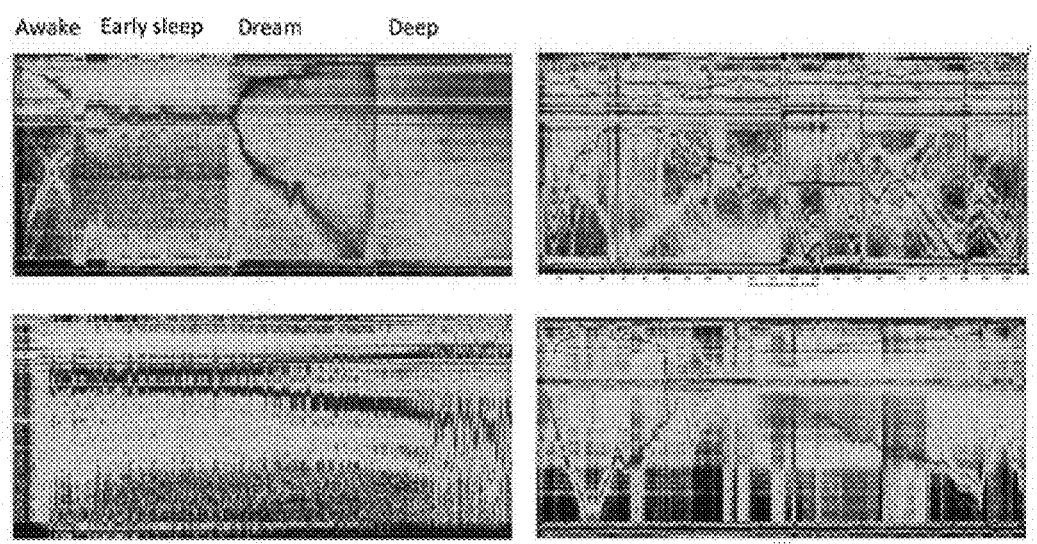
FIG. 9 shows a screenshot of an example of a BAFs representation of a subject according to some embodiments of the present invention.

Sleep monitoring is crucial for the early detection of physical and mental health problems; diagnosis and treatment of insomnia; and diagnosis and monitoring of dementia. Fatigue monitoring is crucial when the brain is engaged in tasks that require fast thinking and response, especially in roles where alertness is essential to performance and safety (e.g. a pilot). FIG. 9 indicates the amount of information that can be obtained using the said BAF. The upper left panel depicts three sleep stages, in which brain activity is vastly different. The activity was recorded from a single person during a single night's sleep. The bottom left panel concentrates on the early sleep stage, demonstrating a different shift from that stage (which is similar to meditation) into the REM or dream stage. The top right panel demonstrates an intense dream and cognitive activity during sleep, looking very similar to the kind of activity that occurs while being awake, e.g. while watching a movie. The bottom right panel indicates the strength of BAF for fatigue monitoring: it depicts the brain activity of a subject briefly falling asleep while watching a movie. The engagement with the movie is clear even when the subject is partially falling asleep, as the line of strong activity behind the (snow-like noise).

Example 6

Figure 10:
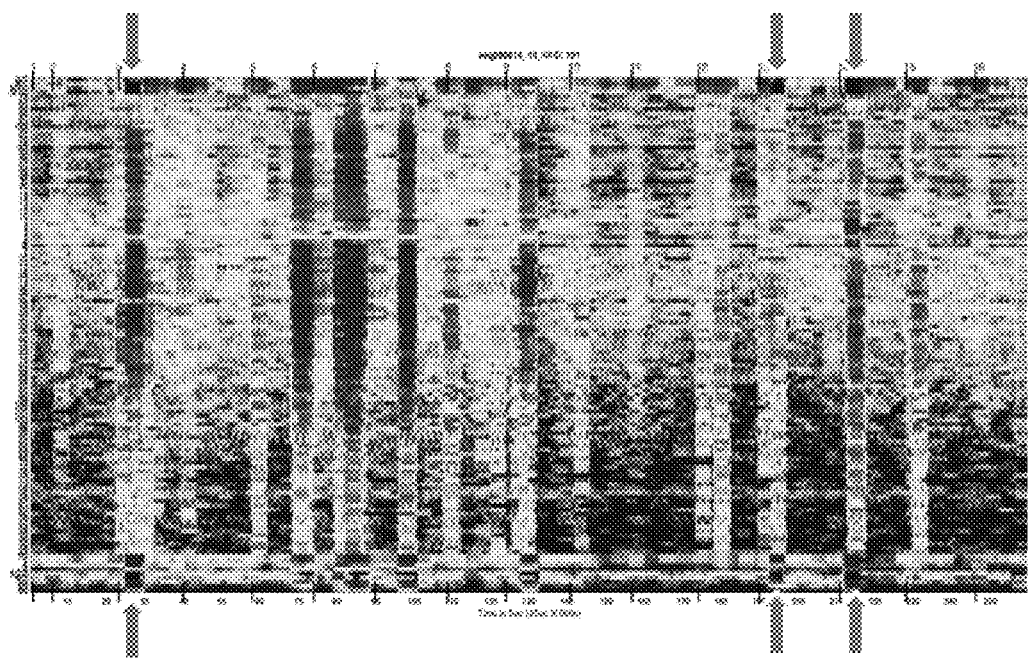
FIG. 10 shows a screenshot of an example of a BAFs representation of a subject according to some embodiments of the present invention.

BAF Representations Obtained from Subjects During a Memory Recall Task and Stress Detection The activity depicted in FIG. 10 is typical during a session of questions and answers, or during stimulus identification. The length and strength of the lines is indicative of the amount of cognitive effort. It is also possible to see stress at the regions pointed to by the arrows. The recording was taken during a company interview. The representation indicates questions which required more cognitive load to respond to (memory or concentration) and in particular show questions which elicited stress in the subject.

Such representation can be useful for lie/stress detection and for automatic (machine induced interrogation). It can also be used for massive teaching such as Coursera, where it is important to observe that the subject is concentrated and focused on the questions. The pattern would look different if the subject had the answer on a piece of paper or contacted a friend to obtain the answer.

If detailed BAF representation is specific to a subject, it may possible to determine the identity of the subject from the specific BAFs. This can be used for authentication and identity management as well as for competency monitoring indicating when the subject is capable of performing the required task: is concentrated, not stressed or otherwise emotionally distracted, is not under the influence of drugs or under threat.

Example 7

BAF Representations Obtained from Subjects Having Abnormal Brain Activity Associated with a Seizure The arrows in FIG. 4 indicate a constant activity of a certain BAF which may be indicative of a constant activity of a certain brain network or region. Such constant activity is not normal and appears to be associated with pre-seizure activity. The two bottom arrows indicate the beginning and end of the abnormal activity of a certain BAF. Using such representation it may be possible to better quantify and study the factors and stimulations which increase the likelihood of such abnormal activity and those which reduce it. This can be useful for intervention, either by suggesting a lifestyle change (relaxation, turning light off, consuming sugar, coffee etc., or meditation, exercise and other state change. It can also suggest better disease management via medications.

Referring to FIG. 3A, an experienced yogi is performing three types of meditation (indicated via the horizontal brackets). After the first two meditations and after the third meditation, the yogi explains what he is doing. A range in BAFs is indicated with the vertical brackets. This collection of BAFs is of associated with awareness. It is clear that one meditation emphasizes only these awareness channels, and it is evident in the activity when the yogi explains what meditation he is doing.

Referring to FIG. 3B, a BAFs representation is shown from an individual in a vegetative state. The BAFs highlights in FIG. 3A are shown, and are not active. However, administration of a stimulus to the individual was able to activate the BAFs associated with awareness for a short period of time.

Example 8

BAF Representations Obtained from Subjects Observing an Advertisement

Figure 11:
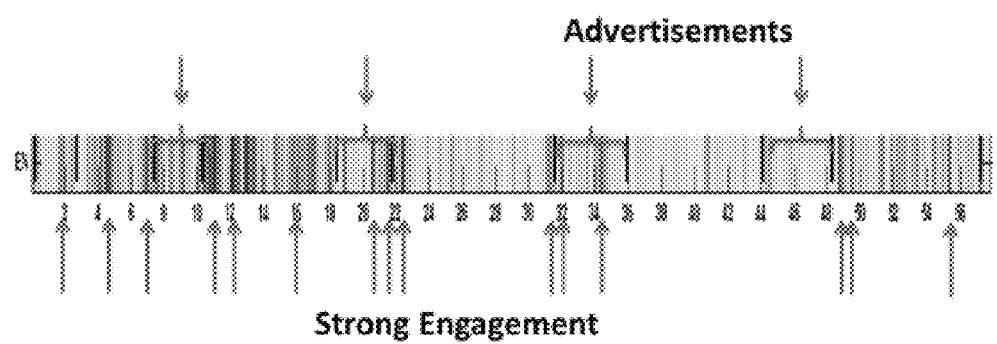
FIG. 11 shows a screenshot of an example of a representation of recording for a brain activity feature of a subject according to some embodiments of the present invention.

In FIG. 11, the summary statistics of a large cohort of subjects is shown. Brain activity of the group was recorded while they were exposed to a TV show (57 minutes) which had several commercial breaks marked by the arrows at the top. In a preferred embodiment, the brain activity as interpreted by the said BAFs and was then clustered into eight clusters of brain activity. The vertical colored lines represent the proportion of subjects which happened to be in the same cluster of brain activity in a specific second of the TV show. The values can change every second. The red lines indicate that the majority of subjects were found to be in the same brain activity cluster at that second. This indicates engagement with the show or the advertisements. Using such representation can be useful for determining the more engaging parts of the show and the advertisements. When such recording is done in a distributed manner in many houses of TV viewers, one can obtain a real time engagement score which can then be used for advertising effectiveness and other media explorations.

Figure 12:
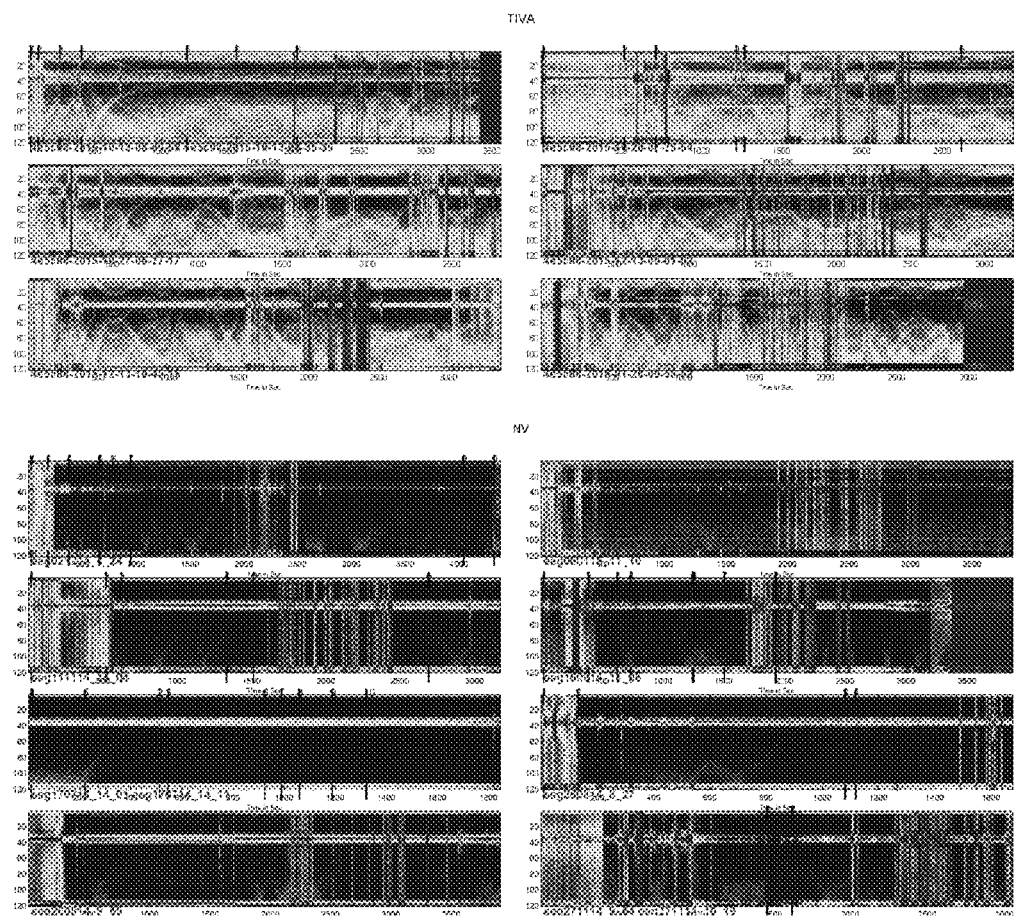
FIG. 12 shows a screenshot of an example of multiple representations of recording for a brain activity feature of a subject according to some embodiments of the present invention.

In FIG. 12, a collection of recordings from two types of anesthesia medications are presented. It is evident that the top 6 recordings represent a very different brain activity as compared to the bottom 8 recordings. This indicates the power of the technique to separate between two anesthesia methods, Total IV vs. Gas.

Example 9

BAF Representations BAFs Obtained in Real Time

FIGS. 2 and 12 illustrate brain activity images constructed based on the real-time processing of the EEG signal based on the full matrix and without the re-scaling. It represents difference in brain activity between two different anesthetic techniques. The first one is called TIVA which is Total IV Anesthesia vs. NV which is inhalation (gas) anesthesia. Both are considered safe and are supposed to provide full anesthesia, however, NV is significantly less costly. The figure demonstrate a strong difference in brain activity between the two anesthesia methods, a difference that would not be seen using the Bispectral index (BIS) monitor.

Example 10

Brain Computer Interface

Figure 13:
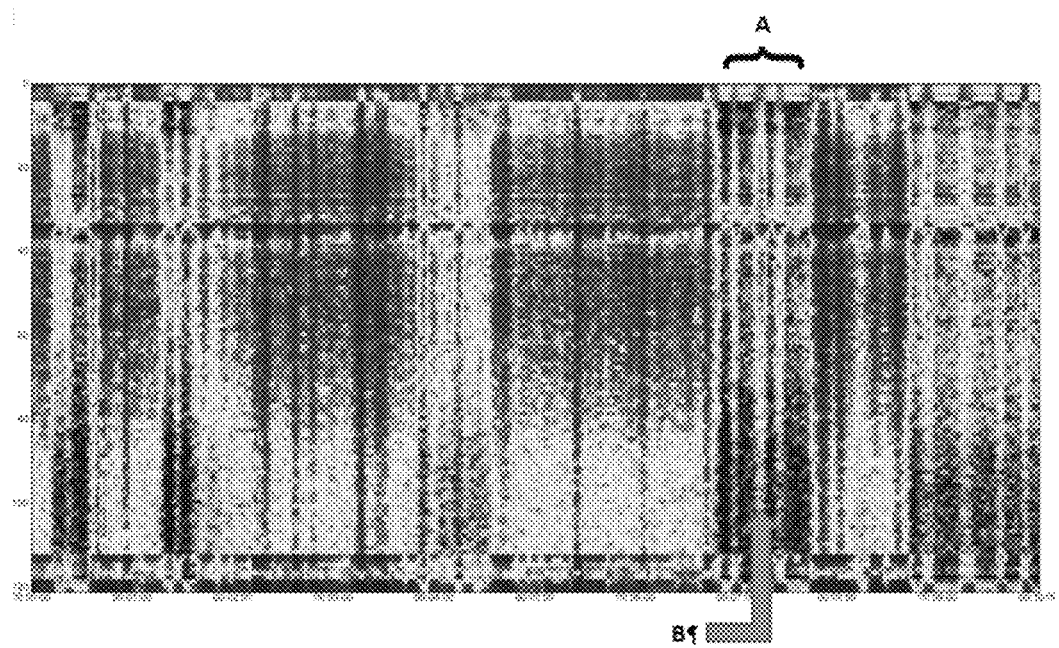
FIG. 13 shows a screenshot of an example of a BAFs representation of a subject according to some embodiments of the present invention.

FIG. 13 shows a BAFs representation from individual entering into a meditative state (as indicated by the horizontal bracket A), and leaves the meditated state. In the Example shown, the brain state in the time period indicated by the horizontal bracket A is associated with the meditative state. The system of the present invention analyzes the specific parameters of the BAFs within the BAFs representation, and applies a machine learning algorithm to detect a brain state associated with the meditative state. The system can then issue a specific command to the individual, once the brain state associated with the meditative state is detected. For example, the individual has ALS, and lacks motor control. The individual enters the meditative state, and the system issues a command for the individual to imagine shooting a ball into a hoop during the meditative state. All activity is performed with the eyes open, so as to make sure that the effects seen are not due to eye movement or being closed. All activity is also performed with background noise (family members speaking and watching the activity) so as to demonstrate the ability to disregard the environment and be fully concentrated in the activity.

Taken together, the data presented in Examples 1-10 show specific predictors for a specific brain state that were present in the BAF representations of human subjects. Further, the predictors for a specific brain state that were present in the BAF representations of human subjects were associated to brain states described in each of these embodiments. Automatic analysis of such BAF representations, to determine specific features related to brain activity which include but are not limited to abnormality, stress, and engagement can be done using state of the art techniques in machine learning and computer vision.

In some embodiments, the inventive specifically programmed computer processors and systems of the present invention can include the use of electronic mobile devices (e.g., smartphones, etc.) in the distributed network environment, communicating over a suitable data communication network (e.g., the Internet, etc.) and utilizing at least one suitable data communication protocol (e.g., IPX/SPX, X.25, AX.25, AppleTalk, TCP/IP (e.g., HTTP), etc.).

Figure 14:
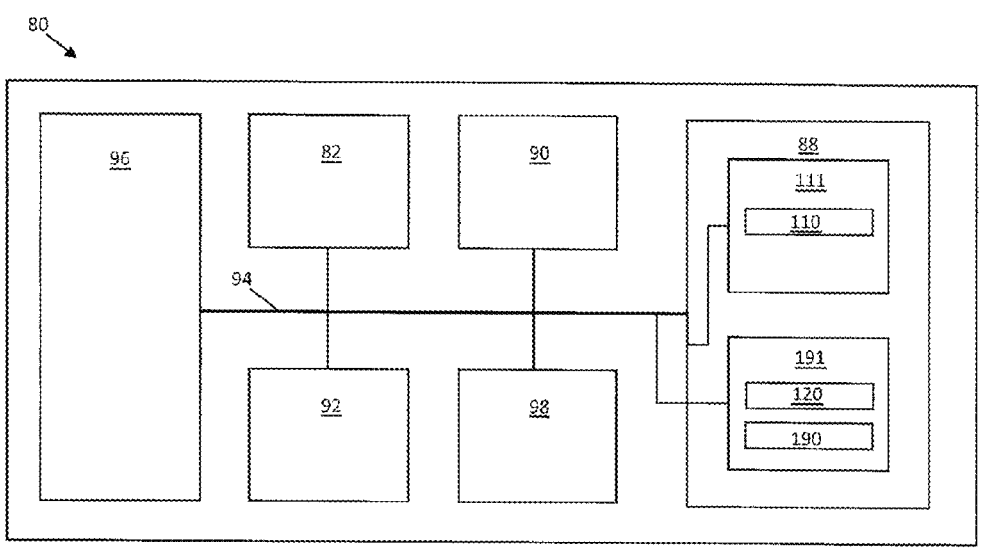
FIG. 14 shows a screenshot of an example of a computer architecture which is specifically programmed according to some embodiments of the present invention.

An exemplary block diagram of a computer which can be specifically programmed in accordance with the present invention is shown in FIG. 14. Computer system 80 includes a processor 82, such as a central processing unit, an input/output interface 90 and support circuitry 92. In certain embodiments, where the computer 80 requires a direct human interface, a display 96 and an input device 98 such as a keyboard, mouse or pointer are also provided. The display 96, input device 98, processor 82, and support circuitry 92 are shown connected to a bus 94 which also connects to a memory 88. Memory 88 includes program storage memory 111 and data storage memory 191. Note that while computer 80 is depicted with direct human interface components display 96 and input device 98, programming of modules and exportation of data can alternatively be accomplished over the interface 90, for instance, where the computer 80 is connected to a network and the programming and display operations occur on another associated computer, or via a detachable input device as is known with respect to interfacing programmable logic controllers.

Program storage memory 111 and data storage memory 191 can each comprise volatile (RAM) and non-volatile (ROM) memory units and can also comprise hard disk and backup storage capacity, and both program storage memory 111 and data storage memory 191 can be embodied in a single memory device or separated in plural memory devices. Program storage memory 111 stores software program modules and associated data, and in particular stores one or more modules 110. Data storage memory 191 stores the data sets representative of the signal data and various software objects utilized in accordance with the present invention.

It is to be appreciated that the computer system 80 can be any computer such as a personal computer, minicomputer, workstation, mainframe, a dedicated controller such as a programmable logic controller, or a combination thereof. While the computer system 80 is shown, for illustration purposes, as a single computer unit, the system can comprise a group/farm of computers which can be scaled depending on the processing load and database size. In certain embodiments, the system and method herein can be operate on a user's computer, for instance, in a user's browser, querying among schedule data that resides on the user's machine, after having been downloaded without query from a networked server computer. However, not all of these components may be required to practice the invention, and variations in the arrangement and type of the components may be made without departing from the spirit or scope of the invention. In some embodiments, the inventive system and method may include a large number of users and/or concurrent transactions. In other embodiments, the instant inventive systems are based on a scalable computer and network architecture that incorporates various strategies for assessing the data, caching, searching, and database connection pooling. An example of the scalable architecture is an architecture that is capable of operating multiple servers that are in real-time communicating with numerous electronic devices of users (e.g., smartphones). In some embodiment, the inventive systems of present invention can host a large number of electronic devices of users (e.g., at least 100; at least 1,000, at least 10,000; at least 100,000; at least 1,000, 000; at least 1,000,000,000, etc.) and/or perform a large number of concurrent actions/transactions (e.g., at least 1,000; at least 10,000; at least 100,000; at least 1,000,000, at least 1,000,000,000, etc.).

The computing device 80 preferably supports an operating system, for example stored in program storage memory 111 and executed by the processor 82 from volatile memory. According to an embodiment of the invention, the operating system contains instructions for executing software routines programmed in accordance with the present invention.

In various alternate embodiments, the present invention may be implemented as a computer program product for use with a computerized computing system. Those skilled in the art will readily appreciate that programs defining the functions defined by the present invention can be written in any appropriate programming language and delivered to a computer in many forms, including but not limited to: (a) information permanently stored on non-writeable storage media (e.g., read-only memory devices such as ROMs or CD-ROM disks); (b) information alterably stored on write-able storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

Figure 15:
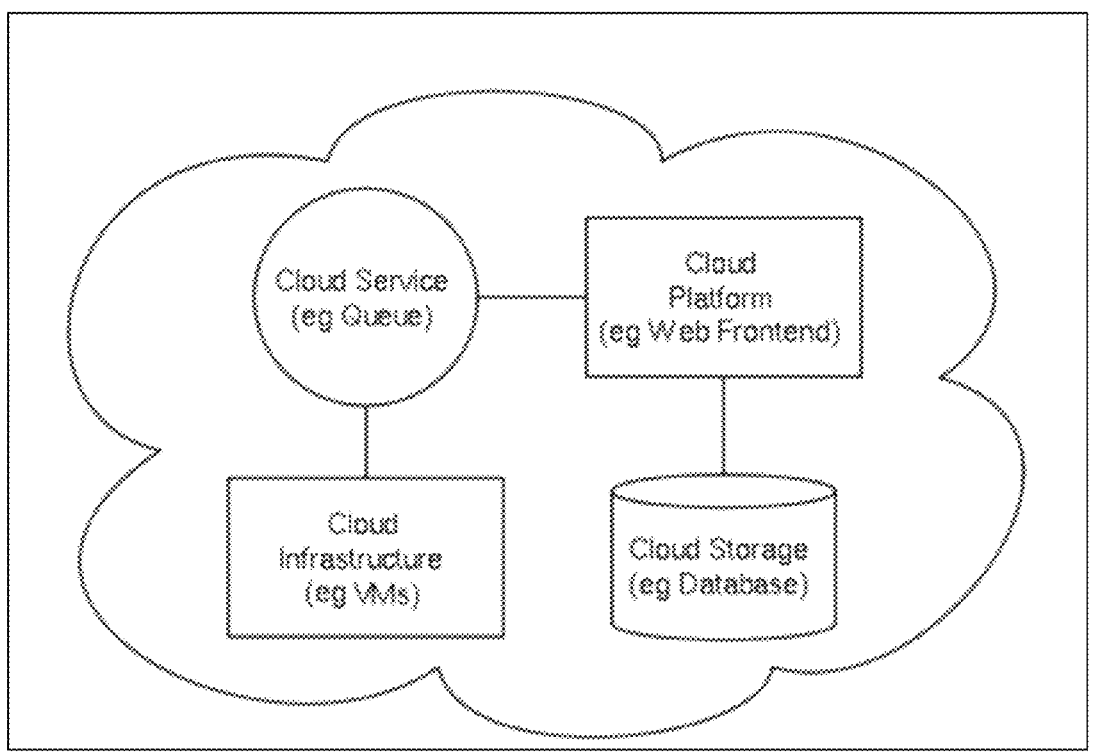
FIG. 15 shows a screenshot of an example of a computer architecture which is specifically programmed according to some embodiments of the present invention.
Figure 16:
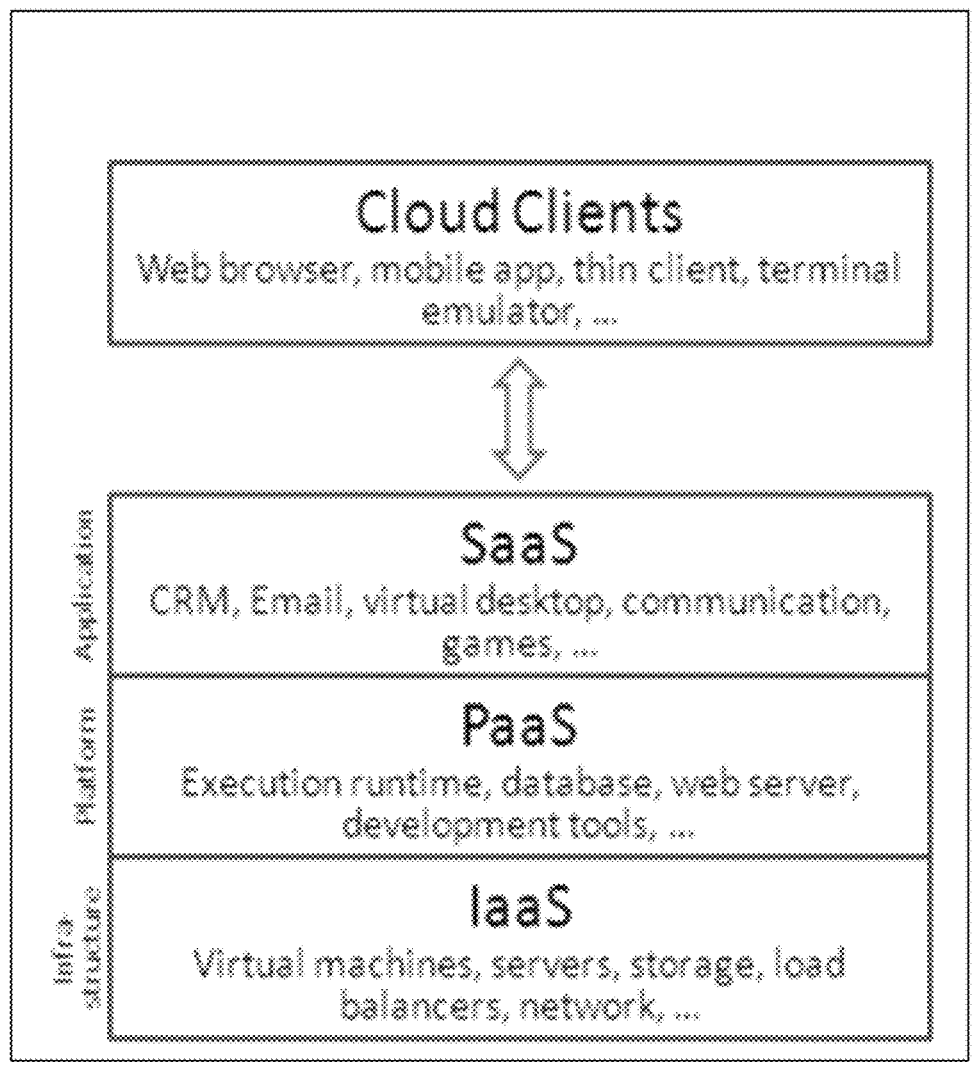
FIG. 16 shows a screenshot of an example of a computer architecture which is specifically programmed according to some embodiments of the present invention.

For purposes of the instant description, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). In some embodiments, the inventive game-operating system offers/manages the cloud computing/architecture as, but not limiting to: infrastructure a service (IaaS), platform as a service (PaaS), and software as a service (SaaS). FIGS. 15 and 16 illustrate schematics of exemplary implementations of the cloud computing/architecture. In some embodiments, the exemplary specifically programmed processor of the present invention is programmed as a cloud-based server which receives, over a computer network, a remotely acquired signal data to analyze such data in accordance with the principles of the present invention and to remotely communicate results of such analysis.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Although the various aspects of the invention have been illustrated above by reference to examples and preferred embodiments, it will be appreciated that the scope of the invention is defined not by the foregoing description but by the following claims properly construed under principles of patent law. While a number of embodiments of the present invention have been described, it is understood that these embodiments are illustrative only, and not restrictive, and that many modifications may become apparent to those of ordinary skill in the art. Further still, the various steps may be carried out in any desired order (and any desired steps may be added and/or any desired steps may be eliminated).

What is claimed is:

1. A method for detection of at least one abnormal electrical brain activity, comprising:
    a) utilizing a first electroencephalographic (EEG) monitoring device having a first set of three electrodes and applying the first set of three electrodes to particular points on a head of each individual of a plurality of individuals, wherein the three electrodes of the first set are:
        1) a first recording electrode,
        2) a second recording electrode, and
        3) a reference electrode;
    b) collecting, by the first EEG monitoring device, at least 100 recordings of electrical signal data representative of brain activity of the plurality of individuals to form recorded electrical data;
    c) utilizing a first processor configured, when executing a first set of software instructions stored in a first non-transient computer-readable hardware storage medium, to perform at least the following operations:
        1) obtaining a pre-determined ordering of a denoised optimal set of wavelet packet atoms, by:
            i) obtaining an optimal set of wavelet packet atoms from the recorded electrical signal data from the recordings from the plurality of individuals, by:
                1) selecting a mother wavelet;
                2) determining an optimal set of wavelet packet atoms, by:
                    a) deconstructing the recorded electrical signal data into a plurality of wavelet packet atoms, using the selected mother wavelet;
                    b) storing the plurality of wavelet packet atoms in at least one first computer data object;
                    c) determining the optimal set of wavelet packet atoms using the pre-determined mother wavelet and storing the optimal set of wavelet packet atoms in at least one second computer data object, wherein the determining is via utilizing a Coifman-Wickerhauser Best Basis algorithm;
            ii) denoising the obtained optimal set of wavelet packet atoms from the recordings from the plurality of individuals;
            iii) reordering the denoised optimal set of wavelet packet atoms from the recorded electrical signal data from the plurality of individuals to obtain a pre-determined ordering of the denoised optimal set of wavelet packet atoms, by determining a minimum path based on:
                1) projecting the recorded electrical signal data onto the denoised optimal set of wavelet packet atoms to obtain a set of projections,
                    wherein a projection is a result of a convolution of an electrical signal in each time window of the signal and a wavelet packet atom;
                2) determining a collection of wire lengths within the set of projections;
                3) storing the collection of wire lengths for the set of projections in at least one third computer data object;
                4) iteratively determining a plurality of (i) orders of the projections, and (ii) respective wire lengths, by:
                    i) determining the wire length between every two projections by at least one of:
                        1) determining either mean or sum of absolute distance of a statistical measure of an energy of each projection from adjacent projections, and
                        2) 1 - a correlation of every two projections onto the wavelet packet atoms; and
                    ii) storing the wire length data in at least one fourth computer data object;
                5) determining, from the plurality of respective wire lengths, a particular order of projections that minimizes either the mean or sum of the wire lengths across the projections, across each time window, and across all individuals within the plurality of individuals;
    d) defining a set of pre-determined normalization factors, and storing the pre-determined normalization factors in at least one fifth computer data object;
    e) utilizing a second EEG monitoring device having a second set of three electrodes and applying the second set of three electrodes to the particular points on a head of a particular individual;

f) collecting, by the second EEG monitoring device, in real-time, a recording of particular electrical signal data representative of brain activity of the particular individual;
g) utilizing a second processor configured, when executing a second set of software instructions stored in a second non-transient computer-readable hardware storage medium, to further perform at least the following additional operations:
   1) projecting, in real time, the collected particular electrical signal data representative of the brain activity of the particular individual onto the pre-determined ordering of the denoised optimal set of wavelet packet atoms to obtain a particular set of projections of the particular individual;
   2) normalizing, in real time, the particular set of projections of the particular individual using the pre-determined set of normalization factors to form a particular set of normalized projections of the particular individual;
   3) applying at least one machine learning algorithm to the particular set of normalized projections of the particular individual to determine, in real time, at least one particular normalized projection in the particular set of normalized projections which corresponds to the at least one abnormal electrical brain activity, wherein the processor is configured to determine the at least one abnormal electrical brain activity from the particular set of normalized projections of the particular individual; and
   4) generating, in real time, an indication of the at least one abnormal electrical brain activity of the particular individual.

2. The method of claim 1,
wherein the second set of software instructions causes the second processor to further perform:
assigning, based on energy of each normalized projection of the particular individual, a plurality of colors to the particular set of normalized projections of the particular individual; and
   wherein the indication comprises an output that is configured to visually illustrate, via a color of the at least one particular normalized projection, when the at least one abnormal electrical brain activity of the particular individual has occurred at a particular time.

3. The method of claim 1, wherein the mother wavelet is selected from the group consisting of: Haar, Coiflet Daubehies, and Meyer wavelet families.

4. The method of claim 1, wherein the second set of three electrodes is located on a forehead of the particular individual.

5. A method for detection of at least one abnormal electrical brain activity, comprising:
utilizing a first electroencephalographic (EEG) monitoring device having a first set of three electrodes and applying the first set of three electrodes to particular points on a head of each individual of a plurality of individuals;
collecting, by the first EEG monitoring device, at least 100 recordings of electrical signal data representative of brain activity of the plurality of individuals to form recorded electrical data:
utilizing a first processor configured, when executing a first set of software instructions stored in a first non-transient computer-readable hardware storage medium, to perform at least the following operations:
   1) obtaining a pre-determined ordering of a denoised optimal set of wavelet packet atoms, by:
      i) obtaining an optimal set of wavelet packet atoms from the recorded electrical signal data from the recordings from the plurality of individuals, by:
         1) selecting a mother wavelet;
         2) determining an optimal set of wavelet packet atoms, by:
            a) deconstructing the recorded electrical signal data into a plurality of wavelet packet atoms, using the selected mother wavelet,
            b) storing the plurality of wavelet packet atoms in at least one first computer data object;
            c) determining the optimal set of wavelet packet atoms using the pre-determined mother wavelet and storing the optimal set of wavelet packet atoms in at least one second computer data object, wherein the determining is via utilizing a Coifman-Wickerhauser Best Basis algorithm;
   2) denoising the obtained optimal set of wavelet packet atoms from the recordings from the plurality of individuals;
   3) reordering the denoised optimal set of wavelet packet atoms from the recorded electrical signal data from the recordings from the plurality of individuals to obtain a pre-determined ordering of the denoised optimal set of wavelet packet atoms, by determining a minimum path based on:
      a) projecting the recorded electrical signal data onto the denoised optimal set of wavelet packet atoms to obtain a set of projections,
      wherein a projection is a result of a convolution of an electrical signal in each time window of the signal and a wavelet packet atom;
      b) determining a collection of wire lengths for every data point within the set of projections;
      c) storing the collection of wire lengths for the set of projections in at least one third computer data object
      d) iteratively determining a plurality of (i) orders of the projections, and (ii) respective wire lengths, by:
         1) determining the wire length between every two projections by at least one of:
            i) determining either mean or sum of absolute distance of a statistical measure of an energy of each projection from adjacent projections, and
            ii) 1 - a correlation of every two projections onto the wavelet packet atoms; and
         2) storing the wire length data in at least one fourth computer data object;
      e) determining, from the plurality of respective wire lengths, a particular order of projections that minimizes either the mean or sum of the wire lengths across the projections, across each time window, and across all individuals within the plurality of individuals; and
      f) defining a set of pre-determined normalization factors, and storing the set of pre-determined normalization factors in at least one fifth computer data object;
utilizing a second EEG monitoring device having a second set of three electrodes and applying the second set of three electrodes to particular points on a head of a particular individual, wherein the three electrodes of the second set are:

1) a first recording electrode,
2) a second recording electrode, and
3) a reference electrode;
collecting, by the second EEG monitoring device, in real-time, a recording of electrical signal data representative of brain activity of the particular individual;
utilizing a second processor configured, when executing a second set of software instructions stored in a second non-transient computer-readable hardware storage medium, to perform at least the following operations:
1) projecting, in real time, the collected particular electrical signal data representative of the brain activity of the particular individual onto the pre-determined ordering of the denoised optimal set of wavelet packet atoms to obtain a particular set of projections of the particular individual;
2) normalizing, in real time, the particular set of projections of the particular individual using the set of pre-determined normalization factors to form a particular set of normalized projections of the particular individual;
3) applying at least one machine learning algorithm to the particular set of normalized projections of the particular individual to determine, in real time, at least one particular normalized projection in the particular set of normalized projections which corresponds to at least one particular abnormal electrical brain activity, wherein the processor is configured to determine the at least one particular abnormal electrical brain activity from the particular set of normalized projections of the particular individual; and
4) generating, in real time, an output associating the at least one particular normalized projection of the particular set of normalized projections of the particular individual to the at least one particular abnormal electrical brain activity.

6. The method of claim 5, wherein the mother wavelet is selected from the group consisting of: Haar, Coiflet Daubehies, and Meyer wavelet families.

7. The method of claim 5, wherein the second set of software instructions causes the second processor to further perform:
assigning, based on energy of each normalized projection of the particular individual, a plurality of colors to the particular set of normalized projections of the particular individual of the particular individual; and
wherein the output comprises a map that is configured to visually illustrate, via a color of the at least one particular normalized projection, when the at least one abnormal electrical brain activity of the particular individual has occurred at a particular time.

8. The method of claim 5, wherein the second set of three electrodes is located on a forehead of the particular individual.

9. A method for determining a state of pain being felt by a particular individual at a particular state of anesthesia, comprising:
a) utilizing a first electroencephalographic (EEG) monitoring device having a first set of three electrodes and applying the first set of three electrodes to particular points on a head of each individual of a plurality of individuals, wherein the three electrodes of the first set are:
1) a first recording electrode,
2) a second recording electrode, and
3) a reference electrode;
b) collecting, by the first EEG monitoring device, at least 100 recordings of electrical signal data representative of brain activity of the plurality of individuals to form recorded electrical data;
c) utilizing a first processor configured, when executing a first set of software instructions stored in a non-transient computer-readable hardware storage medium, to perform at least the following operations:
1) obtaining a pre-determined ordering of a denoised optimal set of wavelet packet atoms, by:
i) obtaining an optimal set of wavelet packet atoms from the recorded electrical signal data from the recordings from the plurality of individuals, by:
1) selecting a mother wavelet;
2) determining an optimal set of wavelet packet atoms, by:
a) deconstructing the recorded into a plurality of wavelet packet atoms, using the selected mother wavelet;
b) storing the plurality of wavelet packet atoms in at least one first computer data object;
c) determining the optimal set of wavelet packet atoms using the pre-determined mother wavelet and storing the optimal set of wavelet packet atoms in at least one second computer data object, wherein the determining is via utilizing a Coifman-Wickerhauser Best Basis algorithm;
ii) denoising the obtained optimal set of wavelet packet atoms from the recordings from the plurality of individuals;
iii) reordering the denoised optimal set of wavelet packet atoms from the recorded electrical signal data from the recordings from the plurality of individuals to obtain a pre-determined ordering of the denoised optimal set of wavelet packet atoms, by determining a minimum path based on:
1) projecting the recorded electrical signal data onto the denoised optimal set of wavelet packet atoms to obtain a set of projections,
wherein a projection is a result of a convolution of an electrical signal in each time window of the signal and a wavelet packet atom;
2) determining a collection of wire lengths for every data point within the set of projections;
3) storing the collection of wire lengths for the set of projections in at least one third computer data object;
4) iteratively determining a plurality of (i) orders of the projections, and (ii) respective wire lengths, by:
i) determining the wire length between every two projections by at least one of:
1) determining either mean or sum of absolute distance of a statistical measure of an energy of each projection from adjacent projections, and
2) 1 - a correlation of every two projections onto the wavelet packet atoms; and
ii) storing the wire length data in at least one fourth computer data object;
5) determining, from the plurality of respective wire lengths, a particular order of projections that minimizes either the mean or sum of the wire lengths across the projections, across each time window, and across all individuals within the plurality of individuals;

d) defining a set of pre-determined normalization factors, and storing the pre-determined normalization factors in at least one fifth computer data object;

e) utilizing a second EEG monitoring device having a second set of three electrodes and applying the second set of three electrodes to the particular points on a head of a particular individual;

f) collecting, by the second EEG monitoring device, in real-time, a recording of particular electrical signal data representative of brain activity of the particular individual;

g) utilizing a second processor configured to further perform at least the following additional operations when executing a second set of software instructions stored in the non-transient computer-readable hardware storage medium:

1) projecting, in real time, the collected particular electrical signal data representative of the brain activity of the particular individual onto the pre-determined ordering of the denoised optimal set of wavelet packet atoms to obtain a particular set of projections of the particular individual;

2) normalizing, in real time, the particular set of projections of the particular individual using the pre-determined set of normalization factors to form a particular set of normalized projections of the particular individual;

3) applying at least one machine learning algorithm to the particular set of normalized projections of the particular individual to determine, in real time, at least one particular normalized projection in the particular set of normalized projections which corresponds to the state of pain being felt by the particular individual at the particular state of anesthesia, wherein the processor is configured to determine the state of pain being felt by the particular individual at the particular state of anesthesia from the particular set of normalized projections of the particular individual; and 4) generating, in real time, an indication of the state of pain being felt by the particular individual at the particular state of anesthesia.

10. The method of claim 9, wherein the mother wavelet is selected from the group consisting of: Haar, Coiflet Daubehies, and Meyer wavelet families.

11. The method of claim 9, wherein the method further comprises:
administering, based on the indication, a dose of an anesthetic to the particular individual.

12. The method of claim 9, wherein the indication is configured to cause a stop in a medical procedure being performed on the particular individual.

13. The method of claim 9, wherein the second set of software instructions causes the second processor to further perform:
assigning, based on energy of each normalized projection of the particular individual, a plurality of colors to the particular set of normalized projections of the particular individual of the particular individual; and
wherein the indication comprises an output that is configured to visually illustrate, via a color of the at least one particular normalized projection, the state of pain being felt by the particular individual at the particular state of anesthesia at a particular time.

14. The method of claim 9, wherein the second set of three electrodes is located on a forehead of the particular individual.

15. A method for determining a state of pain being felt by a particular individual at a particular state of anesthesia, comprising:
utilizing a first electroencephalographic (EEG) monitoring device having a first set of three electrodes and applying the first set of three electrodes to particular points on a head of each individual of a plurality of individuals;

collecting, by the first EEG monitoring device, at least 100 recordings of electrical signal data representative of brain activity of the plurality of individuals to form recorded electrical data;

utilizing a first processor configured, when executing a second set of software instructions stored in a non-transient computer-readable hardware storage medium, to perform at least the following operations:

1) obtaining a pre-determined ordering of a denoised optimal set of wavelet packet atoms, by:
  i) obtaining an optimal set of wavelet packet atoms from the recorded electrical signal data from the recordings from the plurality of individuals, by:
    1) selecting a mother wavelet;
    2) determining an optimal set of wavelet packet atoms, by:
      a) deconstructing the recorded electrical signal data into a plurality of wavelet packet atoms, using the selected mother wavelet;
      b) storing the plurality of wavelet packet atoms in at least one first computer data object;
      c) determining the optimal set of wavelet packet atoms using the pre-determined mother wavelet and storing the optimal set of wavelet packet atoms in at least one second computer data object, wherein the determining is via utilizing a Coifman-Wickerhauser Best Basis algorithm;

2) denoising the obtained optimal set of wavelet packet atoms from the recordings from the plurality of individuals;

3) reordering the denoised optimal set of wavelet packet atoms from the recorded electrical signal data from the recordings from the plurality of individuals to obtain a pre-determined ordering of the denoised optimal set of wavelet packet atoms, by determining a minimum path based on:
  a) projecting the recorded electrical signal data onto the denoised optimal set of wavelet packet atoms to obtain a set of projections,
    wherein a projection is a result of a convolution of an electrical signal in each time window of the signal and a wavelet packet atom;
  b) determining a collection of wire lengths for every data point within the set of projections;
  c) storing the collection of wire lengths for the set of projections in at least one third computer data object;
  d) iteratively, determining a plurality of (i) orders of the projections, and (ii) respective wire lengths, by:
    1) determining the wire length between every two projections by at least one of
      i) determining either mean or sum of absolute distance of a statistical measure of an energy of each projection from adjacent projections, and
      ii) 1 - a correlation of every two projections onto the wavelet packet atoms; and
    2) storing the wire length data in at least one fourth computer data object;

e) determining, from the plurality of respective wire lengths, a particular order of projections that minimizes either the mean or sum of the wire lengths across the projections, across each time window, and across all individuals within the plurality of individuals; and f) defining a set of pre-determined normalization factors, and storing the pre-determined normalization factors in at least one fifth computer data object;

utilizing a second EEG monitoring device having a second set of three electrodes and applying the second set of three electrodes to particular points on a head of a particular individual, wherein the three electrodes of the second set are:
1) a first recording electrode,
2) a second recording electrode, and
3) a reference electrode;

collecting, by the second EEG monitoring device, in real-time, a recording of electrical signal data representative of brain activity of the particular individual;

utilizing a second processor configured, when executing a second set of software instructions stored in a second non-transient computer-readable hardware storage medium, to perform at least the following operations:
1) projecting, in real time, the collected particular electrical signal data representative of the brain activity of the particular individual onto the pre-determined ordering of the denoised optimal set of wavelet packet atoms to obtain a particular set of projections of the particular individual;
2) normalizing, in real time, the particular set of projections of the particular individual using the set of pre-determined normalization factors to form a particular set of normalized projections of the particular individual;
3) applying at least one machine learning algorithm to the particular set of normalized projections of the particular individual to determine, in real time, at least one particular normalized projection in the particular set of normalized projections which corresponds to the state of pain being felt by the particular individual at the particular state of anesthesia, wherein the processor is configured to determine the state of pain being felt by the particular individual at the particular state of anesthesia from the particular set of normalized projections of the particular individual;
4) generating, in real time, an output associating the at least one particular normalized projection of the particular set of normalized projections of the particular individual to the state of pain being felt by the particular individual at the particular state of anesthesia.

16. The method of claim 15, wherein the mother wavelet is selected from the group consisting of: Haar, Coiflet Daubehies, and Meyer wavelet families.

17. The method of claim 15, wherein the method further comprises:
administering, based on the output, a dose of an anesthetic to the particular individual.

18. The method of claim 15, wherein the output is configured to cause a stop in a medical procedure being performed on the particular individual.

19. The method of claim 15, wherein the second set of software instructions causes the second processor to further perform:
assigning, based on energy of each normalized projection of the particular individual, a plurality of colors to the particular set of normalized projections of the particular individual of the particular individual; and
wherein the output comprises a map that is configured to visually illustrate, via a color of the at least one particular normalized projection, the state of pain being felt by the particular individual at the particular state of anesthesia at a particular time.

20. The method of claim 15, wherein the second set of three electrodes is located on a forehead of the particular individual.

* * * * *